United States Patent [19]

Chen et al.

[11] Patent Number: 5,525,513
[45] Date of Patent: Jun. 11, 1996

[54] DNA ENCODING THE HEME-REGULATED EUKARYOTIC INITIATION FACTOR 2α KINASE

[75] Inventors: Jane-Jane Chen, Belmont; Irving M. London, Cambridge, both of Mass.

[73] Assignee: Massachusetts Institute of Technology, Cambridge, Mass.

[21] Appl. No.: 938,782

[22] Filed: Aug. 31, 1992

[30] Foreign Application Priority Data

Mar. 2, 1992 [JP] Japan ................................. 4-081664

[51] Int. Cl.$^6$ ............................ C12N 15/54; C12N 15/63
[52] U.S. Cl. .................. 435/320.1; 536/23.2; 435/172.3; 435/240.1; 935/14; 935/44; 935/46
[58] Field of Search ........................ 536/23.2; 530/350; 435/320.1, 240.2; 935/14, 19, 70, 79

[56] References Cited

U.S. PATENT DOCUMENTS

| | | | |
|---|---|---|---|
| 4,594,319 | 6/1986 | Sharma | 435/188 |
| 4,683,195 | 7/1987 | Mullis et al. | |
| 5,002,874 | 3/1991 | Kaufman | 435/69.1 |

OTHER PUBLICATIONS de Benedetti, et al. 1986. J. Biol. Chem. 261: 338–342.
Becker et al 1991 Proc. Nat. Acad Sci, USA 88: 1968–1972.
Wek et al 1989 Proc. Nat. Acad Sci, USA 86:4579–4583.
Barnes et al. 1990. Proc. Nat. Acad Sci, USA. 87 6679–6683.
Kranz et al. 1990 Proc. Nat. Acad Sci. USA. 87 6629–6633.
Lee et al. 1987 Nature 327 31–35.
Trachsel et al., Proc. Natl. Acad. Sci. USA, vol. 75, pp. 3654–3658, Aug. 1978; "Regulation of Protein Synthesis . . .".
Chen et al., Proc. Natl. Acad. Sci. USA, vol. 88, pp. 315–319, Jan. 1991; "Amino acid microsequencing of internal tryptic . . .".
Chen et al., Proc. Natl. Acad. Sci. USA, vol. 88 pp. 7729–7733, Sep. 1991; "Cloning of the cDNA of the heme-–regulated . . .".
Meurs et al., Cell, vol. 62, pp. 379–390, Jul. 1990; "Molecular Cloning and Characterization of the Human Double–Stranded . . .".
Pal, J., et al., Biochemistry, vol. 30, pp. 2555–2562, 1991; "Tissue Distribution and Immunoreactivity of Heme . . .".
Yang, J., et al., "Structure–function study of heme–regulated eukaryotic initiation factor 2 alpha kinase by site–directed mutagenesis" *J. Cell Biol.* 115:435A (Nov. 1991).
Mendez, R., et al., "Regulation of heme–controlled eukaryotic polypeptide chain initiation factor 2 alpha–subunit kinase of reticulocyte lysates" *J. Biol. Chem.* 267:11500–11507 (5 Jun. 1992).
Chen, J-J., et al., "Disulfide Bond Formation in the Regulation of eIF-2α Kinase by Heme," *J. Biol. Chem.*, 264:9559–9564 (1989).

Cigan, A. M., et al., "Yeast Translation Initiation Suppressor sui2 Encodes the α Subunit of Eukaryotic Initiation Factor 2 and Shares Sequence Identity with the Human α Subunit," *Proc. Natl. Acad. Sci., USA*, 86:2784–2788 (1989).
Dever, T. E., et al., "Phosphorylation of Initiation Factor 2α by Protein Kinase GCN2 Mediates Gene–Specific Translational Control of GCN4 in Yeast," *Cell*, 68, 585–596 (1992).
Ernst, H., et al., "Cloning and Sequencing of Complementary DNAs Encoding the α–Subunit of Translational Initiation Factor eIF-2," *J. Biol. Chem.*, 262:1206–1212 (1987).
Fawcett, T. W., et al., "An Effective Method for Eliminating 'Artifact Banding' When Sequencing Double–Stranded DNA Templates," *Bio Techniques*, 9:46–48 (1990).
Felger, P. L., et al., "Lipofection: A Highly Efficient, Lipid–mediated DNA–Transfection Procedure", *Proc. Natl. Acad. Sci.*, 84:7413–7417 (1987).
Frohman, M. A., et al., "Rapid Production of Full–length cDNAs from Rare Transcripts: Amplification Using a Single Gene–specefic Oligonucleotide Primer," *Proc. Natl. Acad. Sci. USA*, 85, 8998–9002 (1988).
Gallie, D. R., et al., "A Comparison of Eukaryotic Viral 5'–Leader Sequences as Enhancers of mRNA Expression In Vivo," *Nucl. Acids Res.*, 15, 8693–8711 (1987).
Gehrke, L., et al., "In: McCarthy, JEG Post–Transcriptional Regulation of Gene Expression, Series H: Cell Biology, ed. Tuite, M. (Springer Verlag, Berlin)", 49:389–398 (1990).
Hanks, S. K., et al., "The Protein Kinase Family: Conserved Features and Deduced Phylogeny of the Catalytic Domains," *Science*, 241:42–52 (1988).
Maizel, J. V., Jr., et al., "Enhanced Graphic Matrix Analysis of Nucleic Acid and Protein Sequences," *Proc. Natl. Acad. Sci., USA* 78:7665–7669 (1981).

(List continued on next page.)

Primary Examiner—Charles L. Patterson, Jr.
Assistant Examiner—G. E. Bugaisky
Attorney, Agent, or Firm—Arnall Golden & Gregory

[57] ABSTRACT

The cDNA which encodes heme-regulated eIF-2α kinase (HRI) has been cloned from a lambda Zap II cDNa of rabbit reticulocytes. The rabbit HRI cDNA is highly homologous to human HRI and hybridizes to the human HRI DNA under moderately stringent conditions. The rabbit HRI cDNA contains 2729 amino acids. In vitro translation of HRI mRNA transcribed from HRI cDNA yields a 90 kDa polypeptide with eIF-2α kinase activity. Since HRI is a potent inhibitor or protein synthesis, it is anti-proliferative in nature. In addition, the unusually high degree of homology of HRI to three protein kinases involved in the regulation of cell division suggests that HRI plays a direct role in the regulation of cell division. Since regulation of protein synthesis is vital of cell growth and differentiation, the cDNA can be inserted into cells to manipulate proliferation and differentiation, especially of cells that are proliferating in an uncontrolled manner of characterized by arrested differentiation, such as some of the types of cancers. Deletion mutants of HRI cDNA can be constructed that are insensitive to regulation by heme, which should be more effective than native HRI in its anti-viral and anti-proliferative action.

6 Claims, 6 Drawing Sheets

OTHER PUBLICATIONS

Maniatis, T., et al., *Molecular Cloning*, Cold Spring Harbor Laboratory Press (1989).

Miller, A. D., et al., "Improved Retroviral Vectors for Gene Transfer and Expression," *Bio Techniques*, 7:980–990 (1989).

Pathak, V. K., et al., "Generation of a Mutant Form of Protein Synthesis Initiation Factor elf–2 Lacking the Site of Phosphorylation by eIF–2 Kinases," *Mol. Cell. Biol.*, 8:993–995 (1988).

Pearson, W. R., et al., "Improved Tool for Biological Sequence Comparison," *Proc. Natl. Acad. Sci.*, USA, 85:2444–2448 (1988).

Sanger, F., et al., "DNA Sequencing with Chain–terminating Inhibitors," *Proc. Natl. Acad. Sci.*, USA, 74:5463–5467 (1977).

Tzamarias, D., et al., *Cell*, 57:947–954 (1989).

Ullrich, A., et al., "Signal Transduction by Receptors with Tyrosine Kinase Activity," *Cell*, 61:302–212 (1990).

Wilson, J. M., et al., "Implantation of Vascular Grafts Lined With Genetically Modified Endothelial Cells", *Science*, 244:1344–1346 (1980).

```
                                        I                                  II                        III
CaMPK    9/TEEYQLFEEL   GKGAFSVVRR   CVKVLAGQEY    AAKIINTKKL   SARDHQKLER   EARICRLLKH
HRI    166/LNEFEELSIL   GKGGYGRVYK   VRNKLDGQYY    AIKKILIKGA   TKTDCMKVLR   EVKVLAGLQH
Src     60/HEDVSLGELL   CKCNFGEVYK   GTLKDKTP.V    AVRTCKEDLP   .QELKIKFLQ   EAKILKQYDH

IV                                       V
CaMPK    PNIVRLHDSI     SEEGHH....   ..YLIFDLVT    GGELFEDIVA   REYYSEAD..   //..ASHCI
HRI      PNIVGYHTAW     IEHVHVHVQA   DRVPIQLPSL    EVLSDQEEDR   DQYGVKNDA    (138) ATKIF
Src      PNIVKLIGVC     TQRQPV....   ..YIIMELVP    GGDFLSFLRK   RKDELKLKQ.   //..LVRFS

VI                         VII
CaMPK    QQILEAVLHQ     HQMGVVHRDL   KPENULLASK    LKGAAVKLAD   EGLAIEVEGE   QQAW......
HRI      QELVEGVFYI     HNMGIVHRDL   KPRNIFLHGP    DQQ..VKIGD   EGLACADIIQ   KNAARTSRNG
Src      LDVAAGMLYL     EGKNCIHRDL   AARNOLVGEN    NT...LKISD   FGMSRQEDGG   VYSSS.....

VIII                        IX
CaMPK    ....FGFA       GTPGYLSPEV   LRKDPYGKPV    DLWNCGVILY   ILLVGYPPFW   DEDQHRLYQQ
HRI      ERAPTHTSRV     GTCLYASPEQ   LEGSEYDAKS    DMYSVGVILL   ELFQPFGTEM   ERAEVLTGVR
Src      ......GLKQ     IPIKWTAPEA   LNYGRYSSES    DVWSFGILLW   ETFSLGVCPY   PGMTNQQARE

X                                        XI
CaMPK    IKAGAYDFPS     PEWDT.....   VTPEAKDLI     NKMLTINPSK   RITAAEALKH   /210
HRI      AGRIPDSLSK     RCPAQ (26)   FQNSAHVNU     TLQMKIIEQE   REIEELKKQL   /20
Src      QVERGYRMSA     PQN.......   CPEEIFTIM     MKCWDYKPEN   RPKFSDLHKE   /9
```

FIGURE 3

Mouse

Human

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
    ( A ) LENGTH: 2729 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE: N-terminal ( v i ) ORIGINAL SOURCE:
    ( A ) ORGANISM: Rabbit
    ( G ) CELL TYPE: Reticulocytes ( i x ) FEATURE:
    ( A ) NAME/KEY: misc_feature
    ( B ) LOCATION: 113..2149
    ( D ) OTHER INFORMATION: /note="Expression of HRI
        mRNA in Human erythroid cells, using as the
        probe rabbit HRI cDNA from nucleotides 113
        to 2149."

( i x ) FEATURE:
    ( A ) NAME/KEY: misc_feature
    ( B ) LOCATION: 229..249
    ( D ) OTHER INFORMATION: /note="Primer used in the
        amplification of human HRI cDNA sequence
        using the rabbit HRI cDNA sequence."

( i x ) FEATURE:
    ( A ) NAME/KEY: misc_feature
    ( B ) LOCATION: 543..560
    ( D ) OTHER INFORMATION: /note="Primer used in the
        amplification of human HRI cDNA sequence
        using the rabbit HRI cDNA sequence."

( i x ) FEATURE:
    ( A ) NAME/KEY: misc_feature
    ( B ) LOCATION: 448..468
    ( D ) OTHER INFORMATION: /note="Primer used in the
        amplification of human HRI cDNA sequence
        using the rabbit HRI cDNA sequence."

( i x ) FEATURE:
    ( A ) NAME/KEY: misc_feature
    ( B ) LOCATION: 1009..1031
    ( D ) OTHER INFORMATION: /note="Primer used in the
        amplification of a human HRI cDNA sequence
        using the rabbit HRI cDNA sequence."

( x ) PUBLICATION INFORMATION:
    ( A ) AUTHORS: Chen, Jane J.
        London, Irving M.
    ( B ) TITLE: Cloning of the cDNA of the heme-
        regulated eukaryotic initiation factor
        2alpha (eIF- 2alpha)kinase of rabbit reticulocytes:
        Homology to yeast GCN2 protein kinase and human
        double- stranded-RNA-dependent
    ( C ) JOURNAL: Proc. Natl. Acad. Sci. U.S.A.
    ( D ) VOLUME: 88
    ( F ) PAGES: 7729-7733
    ( G ) DATE: September-1991

( x i ) SEQUENCE DESCRIPTION: SEQ ID NO:1:

| | | | | | | |
|---|---|---|---|---|---|---|
| CGCACGGCGC | TCGCGACCCG | GACGCGCGAG | GAGGCGGTCC | CGGAGTCGGG | GAGCTGGCGG | 60 |
| GTGGGCTGTG | GTCCCCGCAT | TTGCGCGCGC | GGGCGCCCGC | GCGTGACCGG | CGATGCTGGG | 120 |
| GGGCAGCGCC | GGGACCCGCG | GGGGCGAAGC | CGAGGGCGAC | GGGGCGGGGG | CGGTGGGGGC | 180 |
| GGTGGCCCCG | CCGCCCGCCA | TCGACTTCCC | CGCTGAGGTG | TCGGATCCCA | AGTATGACGA | 240 |
| GTCGGATGTC | CCGGCAGAGC | TGCAGGTGCT | GAAGGAGCCG | CTGCAGCAGC | CAGCCTTCCC | 300 |

| | | | | | | |
|---|---|---|---|---|---|---|
| CTTCGCCGTC | GCCAACCAGC | TGCTGCTCGT | CTCCCTGCTG | GAGCACCTGA | GTCATGTGCA | 360 |
| CGAGCCAAAC | CCGCTTCGCT | CCAGACAGGT | GTTTAAACTG | CTCTGTCAGA | CCTTCATCAA | 420 |
| AATGGGGCTG | CTGTCTTCCT | TCACCTGCAG | CGACGAGTTT | AGCTCATTGA | GGCTGCATCA | 480 |
| CAACAGAGCT | ATTACGCATC | TGATGAGGTC | CGCCAGAGAG | AGAGTTCGGC | AGGATCCCTG | 540 |
| TGCTGATAAT | TCTCATATCC | AGAAAATCAG | GTCGCGAGAA | GTTGCCTTGG | AAGCACAGAC | 600 |
| CTCACGATAC | TTGAATGAGT | TTGAAGAGCT | CTCCATCCTG | GGGAAGGTG | GCTATGGCCG | 660 |
| AGTGTACAAG | GTCAGGAATA | AATTAGATGG | CCAGTATTAT | GCAATTAAAA | AAATTCTGAT | 720 |
| TAAAGGTGCA | ACTAAAACAG | ATTGCATGAA | GGTATTACGA | GAAGTGAAAG | TGCTGGCGGG | 780 |
| CCTCCAGCAC | CCTAATATCG | TAGGCTATCA | CACCGCGTGG | ATAGAGCATG | TCCACGTTCA | 840 |
| CGTTCAAGCA | GACAGAGTTC | CGATTCAGTT | GCCTTCTCTG | GAAGTGCTCT | CTGACCAGGA | 900 |
| AGAAGACAGA | GATCAATATG | GTGTTAAAAA | TGATGCAAGC | AGCAGCTCAT | CCATTATTTT | 960 |
| CGCTGAGTTC | TCCCCAGAAA | AAGAAAAATC | CTCTGACGAA | TGTGCCGTTG | AGAGTCAGAA | 1020 |
| TAACAAACTG | GTGAACTACA | CCACCAACTT | AGTGGTGAGG | GACACCGGTG | AGTTTGAATC | 1080 |
| GTCCACGGAG | CGCCAAGAGA | ACGGCTCGAT | CGTGGAGCGT | CAGCTACTGT | TCGGGCATAA | 1140 |
| CTCAGACGTA | GAAGAGGATT | TCACGTCCGC | GGAGGAATCT | TCTGAGGAAG | ACTTAAGCGC | 1200 |
| GTTGCGGCAC | ACAGAGGTGC | AGTACCACCT | GATGCTGCAT | ATCCAGATGC | AGCTGTGCGA | 1260 |
| GCTGTCCCTG | TGGGACTGGA | TCGCCGAGAG | GAACAGGCGG | AGCCGAGAGT | GCGTGGACGA | 1320 |
| ATCTGCCTGT | CCTTATGTTA | TGGTCAGTGT | TGCAACAAAA | ATTTTCAAG | AACTGGTGGA | 1380 |
| AGGTGTGTTT | TACATACATA | ACATGGGCAT | CGTGCACAGA | GACCTGAAGC | CTAGAAATAT | 1440 |
| TTTTCTTCAT | GGTCCTGATC | AACAAGTGAA | AATAGGAGAC | TTTGGTCTGG | CCTGCGCCGA | 1500 |
| CATCATCCAG | AAGAATGCGG | CCCGGACCAG | CAGAAACGGG | GAGAGAGCAC | CCACACACAC | 1560 |
| TTCCCGAGTG | GGCACCTGTC | TGTACGCCTC | GCCCGAGCAG | TTGGAAGGAT | CGGAGTATGA | 1620 |
| TGCCAAGTCA | GACATGTACA | GCGTCGGCGT | GATCCTGCTG | GAGCTCTTCC | AGCCCTTCGG | 1680 |
| GACAGAGATG | GAGCGGGCAG | AGGTCCTGAC | GGGCGTGCGA | GCTGGCCGCA | TACCCGACTC | 1740 |
| CCTCAGTAAG | AGGTGCCCGG | CGCAGGCCAA | GTACGTCCAG | CTGCTGACCA | GGAGGAACGC | 1800 |
| GTCCAGCGG | CCGTCCGCCC | TTCAGCTGCT | GCAGAGTGAG | CTCTTCCAGA | ACTCCGCGCA | 1860 |
| TGTTAACCTC | ACCCTACAGA | TGAAGATAAT | AGAGCAGGAA | AGAGAAATCG | AGGAACTCAA | 1920 |
| GAAGCAGCTG | AGCCTCCTCT | CCCAGGCCCG | AGGGGTGAGG | AGTGACAGGC | GAGACGGAGA | 1980 |
| GCTCCCTGCC | TAGCCGTCAC | TCGGCCACGT | CACAGGGGAA | CGTGGACTTG | CACTTGCAGC | 2040 |
| AGTCAACTGG | AATGGACAAT | TTCAAGCCTC | CTGAGGTTCA | GGCGGCATAA | TCCTCACTTG | 2100 |
| GAATCACTCA | GCCCGCATGA | CTCTCCCCTC | ATGCTGCTCT | TCCCGGAGGT | ACCTCCTGGT | 2160 |
| GACCTCCTGG | TGACTGCTCC | CAATTAAACT | TACGCTTTTC | CCTTTCCTAT | TCCGCAAGTC | 2220 |
| CCATTCCTGA | GCCTCCTACC | TAAGCATTAA | CTAAATCTTA | GGTATCGGTC | TCCATTCTTT | 2280 |
| CTCCTTTGAA | TCCTGGCCAC | CTCGCTCCTT | TAGAAGCACA | CTCACTGCCC | CGCCACCACC | 2340 |
| CAAGGCCAGG | CCTGCACCCT | GGCGCAACAG | CTGCCAGTCT | TAGTCCTTAG | CTGCTGCTGC | 2400 |
| TGTTGCCAGA | GACACCTGCT | CCGTTCACTC | CCTCCAGGGT | GGAAGCTCAG | CCTGTGAGCA | 2460 |
| GCGCCTCTGC | TCTCCCCGGC | TGCAGCCCAG | CGCCACTCGG | GCAGGCTTCA | CACGCTCACC | 2520 |
| CCAGGTGGCC | TCGGAACAGC | TGCGACAGCA | TCTCCCCGCA | CCCTTCTGCC | TTCTCAGCAC | 2580 |
| TTGGCTCTCC | AGCCAGCCTC | TCCACTCACT | CGTTTTTGTT | TCCCGGAGCT | GTCTGCCACA | 2640 |
| ATGTTGGCAG | TCTTCATGGA | CTACTGTACG | TGATTCTGCT | GAATTTTAAA | TAAATAAACC | 2700 |

CTGCAAATCA AAAAAAAAA AAAAAAAA                                                   2729

( 2 ) INFORMATION FOR SEQ ID NO:2:

( i ) SEQUENCE CHARACTERISTICS:
        ( A ) LENGTH: 626 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rabbit
        ( G ) CELL TYPE: Reticulocytes ( i x ) FEATURE:
        ( A ) NAME/KEY: Peptide
        ( B ) LOCATION: 166..170
        ( D ) OTHER INFORMATION: /label=P- 56

( i x ) FEATURE:
        ( A ) NAME/KEY: Peptide
        ( B ) LOCATION: 454..459
        ( D ) OTHER INFORMATION: /label=P- 52

( i x ) FEATURE:
        ( A ) NAME/KEY: Peptide
        ( B ) LOCATION: 506..510
        ( D ) OTHER INFORMATION: /label=P- 74

( x i ) SEQUENCE DESCRIPTION: SEQ ID NO:2:

```
Met Leu Gly Gly Ser Ala Gly Thr Arg Gly Gly Glu Ala Glu Gly Asp
 1               5                  10                  15

Gly Ala Gly Ala Val Gly Ala Val Ala Pro Pro Pro Ala Ile Asp Phe
             20                  25                  30

Pro Ala Glu Val Ser Asp Pro Lys Tyr Asp Glu Ser Asp Val Pro Ala
             35                  40                  45

Glu Leu Gln Val Leu Lys Glu Pro Leu Gln Gln Pro Ala Phe Pro Phe
 50                  55                  60

Ala Val Ala Asn Gln Leu Leu Leu Val Ser Leu Leu Glu His Leu Ser
 65                  70                  75                  80

His Val His Glu Pro Asn Pro Leu Arg Ser Arg Gln Val Phe Lys Leu
             85                  90                  95

Leu Cys Gln Thr Phe Ile Lys Met Gly Leu Leu Ser Ser Phe Thr Cys
            100                 105                 110

Ser Asp Glu Phe Ser Ser Leu Arg Leu His His Asn Arg Ala Ile Thr
            115                 120                 125

His Leu Met Arg Ser Ala Arg Glu Arg Val Arg Gln Asp Pro Cys Ala
            130                 135                 140

Asp Asn Ser His Ile Gln Lys Ile Arg Ser Arg Glu Val Ala Leu Glu
145                 150                 155                 160

Ala Gln Thr Ser Arg Tyr Leu Asn Glu Phe Glu Glu Leu Ser Ile Leu
                165                 170                 175

Gly Lys Gly Gly Tyr Gly Arg Val Tyr Lys Val Arg Asn Lys Leu Asp
                180                 185                 190

Gly Gln Tyr Tyr Ala Ile Lys Lys Ile Leu Ile Lys Gly Ala Thr Lys
                195                 200                 205

Thr Asp Cys Met Lys Val Leu Arg Glu Val Lys Val Leu Ala Gly Leu
```

```
                    210                    215                    220
Gln  His  Pro  Asn  Ile  Val  Gly  Tyr  His  Thr  Ala  Trp  Ile  Glu  His  Val
225                 230                      235                              240

His  Val  His  Val  Gln  Ala  Asp  Arg  Val  Pro  Ile  Gln  Leu  Pro  Ser  Leu
                    245                      250                         255

Glu  Val  Leu  Ser  Asp  Gln  Glu  Glu  Asp  Arg  Asp  Gln  Tyr  Gly  Val  Lys
                    260                      265                         270

Asn  Asp  Ala  Ser  Ser  Ser  Ser  Ile  Ile  Phe  Ala  Glu  Phe  Ser  Pro
               275                 280                      285

Glu  Lys  Glu  Lys  Ser  Ser  Asp  Glu  Cys  Ala  Val  Glu  Ser  Gln  Asn  Asn
290                           295                      300

Lys  Leu  Val  Asn  Tyr  Thr  Thr  Asn  Leu  Val  Val  Arg  Asp  Thr  Gly  Glu
305                      310                      315                         320

Phe  Glu  Ser  Ser  Thr  Glu  Arg  Gln  Glu  Asn  Gly  Ser  Ile  Val  Glu  Arg
                    325                      330                         335

Gln  Leu  Leu  Phe  Gly  His  Asn  Ser  Asp  Val  Glu  Glu  Asp  Phe  Thr  Ser
                    340                      345                         350

Ala  Glu  Glu  Ser  Ser  Glu  Glu  Asp  Leu  Ser  Ala  Leu  Arg  His  Thr  Glu
               355                      360                      365

Val  Gln  Tyr  His  Leu  Met  Leu  His  Ile  Gln  Met  Gln  Leu  Cys  Glu  Leu
     370                      375                      380

Ser  Leu  Trp  Asp  Trp  Ile  Ala  Glu  Arg  Asn  Arg  Arg  Ser  Arg  Glu  Cys
385                      390                      395                         400

Val  Asp  Glu  Ser  Ala  Cys  Pro  Tyr  Val  Met  Val  Ser  Val  Ala  Thr  Lys
                    405                      410                         415

Ile  Phe  Gln  Glu  Leu  Val  Glu  Gly  Val  Phe  Tyr  Ile  His  Asn  Met  Gly
                    420                      425                         430

Ile  Val  His  Arg  Asp  Leu  Lys  Pro  Arg  Asn  Ile  Phe  Leu  His  Gly  Pro
               435                      440                      445

Asp  Gln  Gln  Val  Lys  Ile  Gly  Asp  Phe  Gly  Leu  Ala  Cys  Ala  Asp  Ile
     450                      455                      460

Ile  Gln  Lys  Asn  Ala  Ala  Arg  Thr  Ser  Arg  Asn  Gly  Glu  Arg  Ala  Pro
465                      470                      475                         480

Thr  His  Thr  Ser  Arg  Val  Gly  Thr  Cys  Leu  Tyr  Ala  Ser  Pro  Glu  Gln
                    485                      490                         495

Leu  Glu  Gly  Ser  Glu  Tyr  Asp  Ala  Lys  Ser  Asp  Met  Tyr  Ser  Val  Gly
               500                      505                      510

Val  Ile  Leu  Leu  Glu  Leu  Phe  Gln  Pro  Phe  Gly  Thr  Glu  Met  Glu  Arg
     515                      520                      525

Ala  Glu  Val  Leu  Thr  Gly  Val  Arg  Ala  Gly  Arg  Ile  Pro  Asp  Ser  Leu
     530                      535                      540

Ser  Lys  Arg  Cys  Pro  Ala  Gln  Ala  Lys  Tyr  Val  Gln  Leu  Leu  Thr  Arg
545                      550                      555                         560

Arg  Asn  Ala  Ser  Gln  Arg  Pro  Ser  Ala  Leu  Gln  Leu  Leu  Gln  Ser  Glu
                    565                      570                         575

Leu  Phe  Gln  Asn  Ser  Ala  His  Val  Asn  Leu  Thr  Leu  Gln  Met  Lys  Ile
               580                      585                      590

Ile  Glu  Gln  Glu  Arg  Glu  Ile  Glu  Glu  Leu  Lys  Lys  Gln  Leu  Ser  Leu
     595                      600                      605

Leu  Ser  Gln  Ala  Arg  Gly  Val  Arg  Ser  Asp  Arg  Arg  Asp  Gly  Glu  Leu
     610                      615                      620

Pro  Ala
625
```

( 2 ) INFORMATION FOR SEQ ID NO:3:

( i ) SEQUENCE CHARACTERISTICS:
        ( A ) LENGTH: 76 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:3:

```
Thr Glu Glu Tyr Gln Leu Phe Glu Glu Leu Gly Lys Gly Ala Phe Ser
 1               5                  10                  15

Val Val Arg Arg Cys Val Lys Val Leu Ala Gly Gln Glu Tyr Ala Ala
            20                  25                  30

Lys Ile Ile Asn Thr Lys Lys Leu Ser Ala Arg Lys His Gln Lys Leu
        35                  40                  45

Glu Arg Glu Ala Arg Ile Cys Arg Leu Leu Lys His Pro Asn Ile Val
    50                  55                  60

Arg Leu His Asp Ser Ile Ser Glu Glu Gly His His
65                  70                  75
```

( 2 ) INFORMATION FOR SEQ ID NO:4:

( i ) SEQUENCE CHARACTERISTICS:
        ( A ) LENGTH: 26 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:4:

```
Tyr Leu Ile Phe Asp Leu Val Thr Gly Gly Glu Leu Phe Glu Asp Ile
 1               5                  10                  15

Val Ala Arg Glu Tyr Tyr Ser Glu Ala Asp
            20                  25
```

( 2 ) INFORMATION FOR SEQ ID NO:5:

( i ) SEQUENCE CHARACTERISTICS:
        ( A ) LENGTH: 59 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:5:

```
Ala Ser His Cys Ile Gln Gln Ile Leu Glu Ala Val Leu His Cys His
 1               5                  10                  15

Gln Met Gly Val Val His Arg Asp Leu Lys Pro Glu Asn Ile Leu Leu
            20                  25                  30

Ala Ser Lys Leu Lys Gly Ala Ala Val Lys Leu Ala Asp Phe Gly Leu
        35                  40                  45

Ala Ile Glu Val Glu Gly Glu Gln Gln Ala Trp
    50                  55
```

( 2 ) INFORMATION FOR SEQ ID NO:6:

( i ) SEQUENCE CHARACTERISTICS:
        ( A ) LENGTH: 69 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:6:

| Phe | Gly | Phe | Ala | Gly | Thr | Pro | Gly | Tyr | Leu | Ser | Pro | Glu | Val | Leu | Arg |
|---|---|---|---|---|---|---|---|---|---|---|---|---|---|---|---|
| 1 | | | | 5 | | | | | 10 | | | | | 15 | |
| Lys | Asp | Pro | Tyr | Gly | Lys | Pro | Val | Asp | Leu | Trp | Trp | Cys | Gly | Val | Ile |
| | | | 20 | | | | 25 | | | | | 30 | | | |
| Leu | Tyr | Ile | Leu | Leu | Val | Gly | Tyr | Pro | Pro | Phe | Trp | Asp | Glu | Asp | Gln |
| | | 35 | | | | | 40 | | | | | 45 | | | |
| His | Arg | Leu | Tyr | Gln | Gln | Ile | Lys | Ala | Gly | Ala | Tyr | Asp | Phe | Pro | Ser |
| | 50 | | | | | 55 | | | | | 60 | | | | |
| Pro | Glu | Trp | Asp | Thr | | | | | | | | | | | |
| 65 | | | | | | | | | | | | | | | |

( 2 ) INFORMATION FOR SEQ ID NO:7:

( i ) SEQUENCE CHARACTERISTICS:
( A ) LENGTH: 29 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:7:

| Val | Thr | Pro | Glu | Ala | Lys | Asp | Leu | Leu | Asn | Lys | Met | Leu | Thr | Ile | Asn |
|---|---|---|---|---|---|---|---|---|---|---|---|---|---|---|---|
| 1 | | | | 5 | | | | | 10 | | | | | 15 | |
| Pro | Ser | Lys | Arg | Ile | Thr | Ala | Ala | Glu | Ala | Leu | Lys | His | | | |
| | | | 20 | | | | | 25 | | | | | | | |

( 2 ) INFORMATION FOR SEQ ID NO:8:

( i ) SEQUENCE CHARACTERISTICS:
( A ) LENGTH: 28 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:8:

| His | Glu | Asp | Val | Ser | Leu | Gly | Glu | Leu | Leu | Gly | Lys | Gly | Asn | Phe | Gly |
|---|---|---|---|---|---|---|---|---|---|---|---|---|---|---|---|
| 1 | | | | 5 | | | | | 10 | | | | | 15 | |
| Glu | Val | Tyr | Lys | Gly | Thr | Leu | Lys | Asp | Lys | Thr | Pro | | | | |
| | | | 20 | | | | | 25 | | | | | | | |

( 2 ) INFORMATION FOR SEQ ID NO:9:

( i ) SEQUENCE CHARACTERISTICS:
( A ) LENGTH: 10 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:9:

| Ala | Val | Lys | Thr | Cys | Lys | Glu | Asp | Leu | Pro |
|---|---|---|---|---|---|---|---|---|---|
| 1 | | | | 5 | | | | | 10 |

( 2 ) INFORMATION FOR SEQ ID NO:10:

( i ) SEQUENCE CHARACTERISTICS:
( A ) LENGTH: 35 amino acids
( B ) TYPE: amino acid ( C ) STRANDEDNESS: unknown
( D ) TOPOLOGY: unknown ( i i ) MOLECULE TYPE: peptide ( x i ) SEQUENCE DESCRIPTION: SEQ ID NO:10:

| Gln | Glu | Leu | Lys | Ile | Lys | Phe | Leu | Gln | Glu | Ala | Lys | Ile | Leu | Lys | Gln |
|---|---|---|---|---|---|---|---|---|---|---|---|---|---|---|---|
| 1 | | | | 5 | | | | | 10 | | | | | 15 | |

| Tyr | Asp | His | Pro | Asn | Leu | Val | Lys | Leu | Ile | Gly | Val | Cys | Thr | Gln | Arg |
|---|---|---|---|---|---|---|---|---|---|---|---|---|---|---|---|
| | | | 20 | | | | | 25 | | | | | 30 | | |

| Gln | Pro | Val |
|---|---|---|
| | | 35 |

( 2 ) INFORMATION FOR SEQ ID NO:11:

( i ) SEQUENCE CHARACTERISTICS:
( A ) LENGTH: 27 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:11:

| Tyr | Ile | Ile | Met | Glu | Leu | Val | Pro | Gly | Gly | Asp | Phe | Leu | Ser | Phe | Leu |
|---|---|---|---|---|---|---|---|---|---|---|---|---|---|---|---|
| 1 | | | | 5 | | | | | 10 | | | | | 15 | |

| Arg | Lys | Arg | Lys | Asp | Glu | Leu | Lys | Leu | Lys | Gln |
|---|---|---|---|---|---|---|---|---|---|---|
| | | | 20 | | | | | 25 | | |

( 2 ) INFORMATION FOR SEQ ID NO:12:

( i ) SEQUENCE CHARACTERISTICS:
( A ) LENGTH: 37 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:12:

| Leu | Val | Arg | Phe | Ser | Leu | Asp | Val | Ala | Ala | Gly | Met | Leu | Tyr | Leu | Glu |
|---|---|---|---|---|---|---|---|---|---|---|---|---|---|---|---|
| 1 | | | | 5 | | | | | 10 | | | | | 15 | |

| Gly | Lys | Asn | Cys | Ile | His | Arg | Asp | Leu | Ala | Ala | Arg | Asn | Cys | Leu | Val |
|---|---|---|---|---|---|---|---|---|---|---|---|---|---|---|---|
| | | | 20 | | | | | 25 | | | | | 30 | | |

| Gly | Glu | Asn | Asn | Thr |
|---|---|---|---|---|
| | | | 35 | |

( 2 ) INFORMATION FOR SEQ ID NO:13:

( i ) SEQUENCE CHARACTERISTICS:
( A ) LENGTH: 20 amino acids
( B ) TYPE: amino acid
( C ) STRANDEDNESS: unknown
( D ) TOPOLOGY: unknown ( i i ) MOLECULE TYPE: peptide ( x i ) SEQUENCE DESCRIPTION: SEQ ID NO:13:

| Leu | Lys | Ile | Ser | Asp | Phe | Gly | Met | Ser | Arg | Gln | Glu | Asp | Gly | Gly | Val |
|---|---|---|---|---|---|---|---|---|---|---|---|---|---|---|---|
| 1 | | | | 5 | | | | | 10 | | | | | 15 | |

| Tyr | Ser | Ser | Ser |
|---|---|---|---|
| | | | 20 |

( 2 ) INFORMATION FOR SEQ ID NO:14:

( i ) SEQUENCE CHARACTERISTICS:

(A) LENGTH: 67 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:14:

```
Gly Leu Lys Gln Ile Pro Ile Lys Trp Thr Ala Pro Phe Ala Leu Asn
 1               5                  10                  15
Tyr Gly Arg Tyr Ser Ser Glu Ser Asp Val Trp Ser Phe Gly Ile Leu
            20                  25                  30
Leu Trp Glu Thr Phe Ser Leu Gly Val Cys Pro Tyr Pro Gly Met Thr
        35                  40                  45
Asn Gln Gln Ala Arg Glu Gln Val Glu Arg Gly Tyr Arg Met Ser Ala
        50                  55                  60
Pro Gln Asn
65
```

(2) INFORMATION FOR SEQ ID NO:15:

(i) SEQUENCE CHARACTERISTICS:
(A) LENGTH: 29 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:15:

```
Cys Pro Glu Glu Ile Phe Thr Ile Met Met Lys Cys Trp Asp Tyr Lys
 1               5                  10                  15
Pro Glu Asn Arg Pro Lys Phe Ser Asp Leu His Lys Glu
            20                  25
```

DNA ENCODING THE HEME-REGULATED EUKARYOTIC INITIATION FACTOR 2α KINASE

BACKGROUND OF THE INVENTION

The United States government has rights in this invention by virtue of grants from the National Institutes of Health, DK 16272 and GM 42504 and from the National Science Foundation, DMB-890538.

This application claims priority to Japanese patent application No. 4-81664 filed Mar. 2, 1992.

The present invention is an isolated nucleic acid sequence encoding the heme-regulated eukaryotic initiation factor 2α, kinase, and methods of use thereof in inhibition of cellular proliferation.

Heme controls the synthesis of protein in reticulocytes. In heme-deficiency, there is diminished initiation of protein synthesis with disaggregation of polyribosomes. The principal mechanism of the inhibition of initiation of protein synthesis is the phosphorylation of the α-subunit of the eukaryotic initiation factor 2, eIF-2e. In addition to heme-deficiency, oxidized glutathione (GSSG) and low levels of double stranded RNA inhibit initiation by promoting phosphorylation of eIF-2α.

The translation of mRNA in eukaryotic cells occurs in the cytoplasm. In the first step of initiation, free 80 S ribosomes are in equilibrium with their 40 S and 60 S subunits. In the presence of eIF-3, 40 S subunits bind the eIF-3and eIF-4C to form a 43 S ribosomal complex; the binding of eIF-3 and eIF-4C to the 40 S subunit inhibits the joining of the 60 S subunit.

In the next step, eIF-2 binds GTP and the initiator tRNA, Met-tRNA$_f$, in a ternary complex. The binding by eIF-2 is specific for both guanine nucleotides and for Met-tRNA$_f$. The ternary complex now binds to the 43 S ribosomal complex to form the 43 S preinitiation complex. The 43 S preinitiation complex binds mRNA in an ATP-dependent reaction in which eIF-4A, eIF-4B, and eIF-4F form a complex with the mRNA. The product of the binding of mRNA to the 43 S structure is bound close to the ribosome and the AUG initiator codon is downstream from the cap structure.

The joining of the 48 S preinitiation complex and the 60 S subunit is catalyzed by eIF-5 which has a ribosome-dependent GTPase activity. The joining reaction is accompanied by the release of the initiation factors eIF-3 and eIF-4C, eIF-2 is translocated to 60 S subunit as a binary complex, eIF2-GDP. The product of the joining reaction is the 80 S initiation complex. Formation of the active 80 S initiation complex is the final step in initiation. The Met-tRNA$_f$ is positioned in the P (peptidyl) site on the ribosome for the start of polypeptide elongation.

The sequence of steps in the process of initiation affords several opportunities for regulation. These include the recycling of eIF-2 after its release as the eIF-2-GDP complex; the formation of the ternary complex; and the relative affinities of mRNAs for eIF-2 and for eIF-4A, -4B, and -4F in determining the relative rates of translation of the mRNAs.

A schematic summary of eukaryotic initiation is shown in FIG. 1. Heme-deficiency inhibited initiation of protein synthesis is characterized by a brief period of control linear synthesis, followed by an abrupt decline in this rate and by disaggregation of polyribosomes, associated with a decrease in the formation of the eIF-2-Met-tRNA$_f$-GTP ternary complex and the 40 S-eIF-2Met-tRNA$_f$-GTP 43 S initiation complex. The fundamental mechanism for the inhibition is the activation of cAMP independent protein kinases that specifically phosphorylate the 38-kDa α-subunit of eIF-2 (eIF-2α). Dephosphorylation of eIF-2α accompanies the recovery of protein synthesis upon addition of hemin to inhibited heme-deficient lysates.

The heme-regulated eukaryotic initiation factor 2α (eIF-2α) kinase, also called heme-regulated inhibitor (HRI), plays a major role in this process. HRI is a cAMP-independent protein kinase that specifically phosphorylates the e subunit (eIF-2α) of the eukaryotic initiation factor 2 (eIF-2). Phosphorylation of eIF-2α in reticulocyte lysates results in the binding and sequestration of reversing factor RF, also designated as guanine nucleotide exchange factor or eIF-2B, in a RF-eIF-2(αP) complex; the unavailability of RF, which is required for the exchange of GTP for GDP in the recycling of eIF-2 and in the formation of the eIF-2-Met-tRNA$_f$-GTP ternary complex, resulting in the cessation of the initiation of protein synthesis.

Although the mechanism of regulation of protein synthesis by HRI has been extensively studied, little is known about the structure and regulation of HRI itself. Chen, J.-J., et al., *Proc. Natl. Acad. Sci.*, USA 88:315–319 (1991) previously reported the amino acid sequences of three tryptic peptides of heme-reversible HRI. HRI peptide P-52 contains the sequence Asp-Phe-Gly, which is the most highly conserved short stretch in conserved domain VII of protein kinases as presented by Hanks, Quinn, and Hunter, *Science* 241:42–52 (1988). The N-terminal 14 amino acids of HRI peptide P-74 show 50-60% identity to the conserved domain IX of kinase-related transforming proteins. These findings are consistent with the autokinase and eIF-2α kinase activities of HRI. As reported by Pal et al., *Biochem.* 30:2555-2562 (1991), this protein appears to be erythroid-specific and antigenically different in different species.

In view of the activity and relationships of HRI to other protein kinases involved in cellular transformation, it would be advantageous to have the nucleic acid sequence encoding HRI. However, since the gene is only expressed during a very limited time period, i.e., during erythroid differentiation, and in an extremely minuscule amount, this was not a simple process. Moreover, even though three peptides isolated by tryptic digest had been sequenced, it was not clear if these were from HRI or from a contaminant of the HRI preparation. Obtaining a library containing a full length HRI cDNA is also difficult.

It is therefore an object of the present invention to provide a cDNA sequence encoding HRI.

It is a further object of the present invention to provide methods for expression of HRI in mammalian cells.

It is still another object of the present invention to provide methods of use of the isolated DNA sequence encoding HRI to inhibit cell proliferation, by inhibiting protein synthesis, especially of transformed cells and in diseases such as psoriasis.

It is another object of the present invention to provide methods of use of the sequence encoding HRI and dsI to induce cellular differentiation and treat cancers involving arrested differentiation.

SUMMARY OF THE INVENTION

The cDNA which encodes heme-regulated eIF-2α kinase (HRI) has been cloned from a lambda Zap II cDNA library of rabbit reticulocytes. The rabbit HRI cDNA is highly homologous to human HRI and hybridizes to the human HRI DNA under moderately stringent conditions. The rabbit HRI cDNA contains 2729 nucleotides and encodes 626 amino acids. In vitro translation of HRI mRNA transcribed from HRI cDNA yields a 90 kDa polypeptide with eIF-2α kinase activity. This 90 kDa polypeptide is recognized by an anti-HRI non-species specific monoclonal antibody. These properties are characteristic of authentic HRI.

Since HRI is a potent inhibitor of protein synthesis, it is anti-proliferative in nature. In addition, the unusually high degree of homology of HRI to three protein kinases involved in the regulation of cell division suggests that HRI may play a direct role in the regulation of cell division. The availability of HRI cDNA provides a means to study the regulation and the structure and function relationship of HRI. Furthermore, since regulation of protein synthesis is vital for cell growth and differentiation, the cDNA can be inserted into cells to manipulate proliferation and differentiation, especially of cells that are proliferating in an uncontrolled manner or characterized by arrested differentiation, such as some of the types of cancers.

Initiation of protein synthesis can also be regulated by another eIF-2α kinase which is activated by double-stranded RNA (dsI). Both HRI and dsI phosphorylate eIF-2α at the same site. However, dsI is induced by interferon and represents an interferon mediated response to viral infection. Since HRI and dsI are eIF-2α kinases, they are both antiviral in nature, but mechanisms of inactivating dsI by viruses should not affect HRI activity. Therefore, when introduced into the proper target, HRI should be as potent or more potent than dsI in its anti-viral action.

Deletion mutants of HRI cDNA can be constructed that are insensitive to regulation by heme. This heme-insensitive HRI should be more effective than native HRI in its antiviral and anti-proliferative action.

BRIEF DESCRIPTION OF THE DRAWINGS

FIG. 3 is an alignment of the conserved catalytic domains of HRI residue 167–275, 414–551, and 578–606 of Sequence ID No. 2) with other protein kinases. The portion of CaMPK are divided by one of more dots indicating breaks in the conserved sequence. A sequence indentification number has been assigned to each consecutive portion, respectively. Accordingly, the amino acid sequences of CaMPK set forth in FIG. 3 are Sequence ID No. 3, Sequence ID No. 4, Sequence ID No. 5, Sequence ID No. 6, and Sequence ID No. 7, and the amino acid sequences of Src set forth in FIG. 3 are Sequence ID No. 8, Sequence ID No. 9, Sequence ID No. 10, Sequence ID No. 11, Sequence ID No. 12, Sequence ID No. 13, Sequence ID No. 14, and Sequence ID No. 15.

The conserved catalytic domains are indicated by the Roman numerals (I to XI). The conserved invariant amino acid residues are shown as black boxes with white letters. The semi-conserved amino acid residues of similar structure are shown in white boxes. Small gaps are shown by dots ( ·· ). There is an insertion of 138 amino acids in HRI between domains V and VI as indicated by {138}. There is an intersection of 26 amino acids in HRI between domains X and XI as indicated by {26}. The additional amino acids beyond the conserved domains are indicated by the numbers on both N- and C- termini. Single letter code of amino acids is used.

Figure 1:
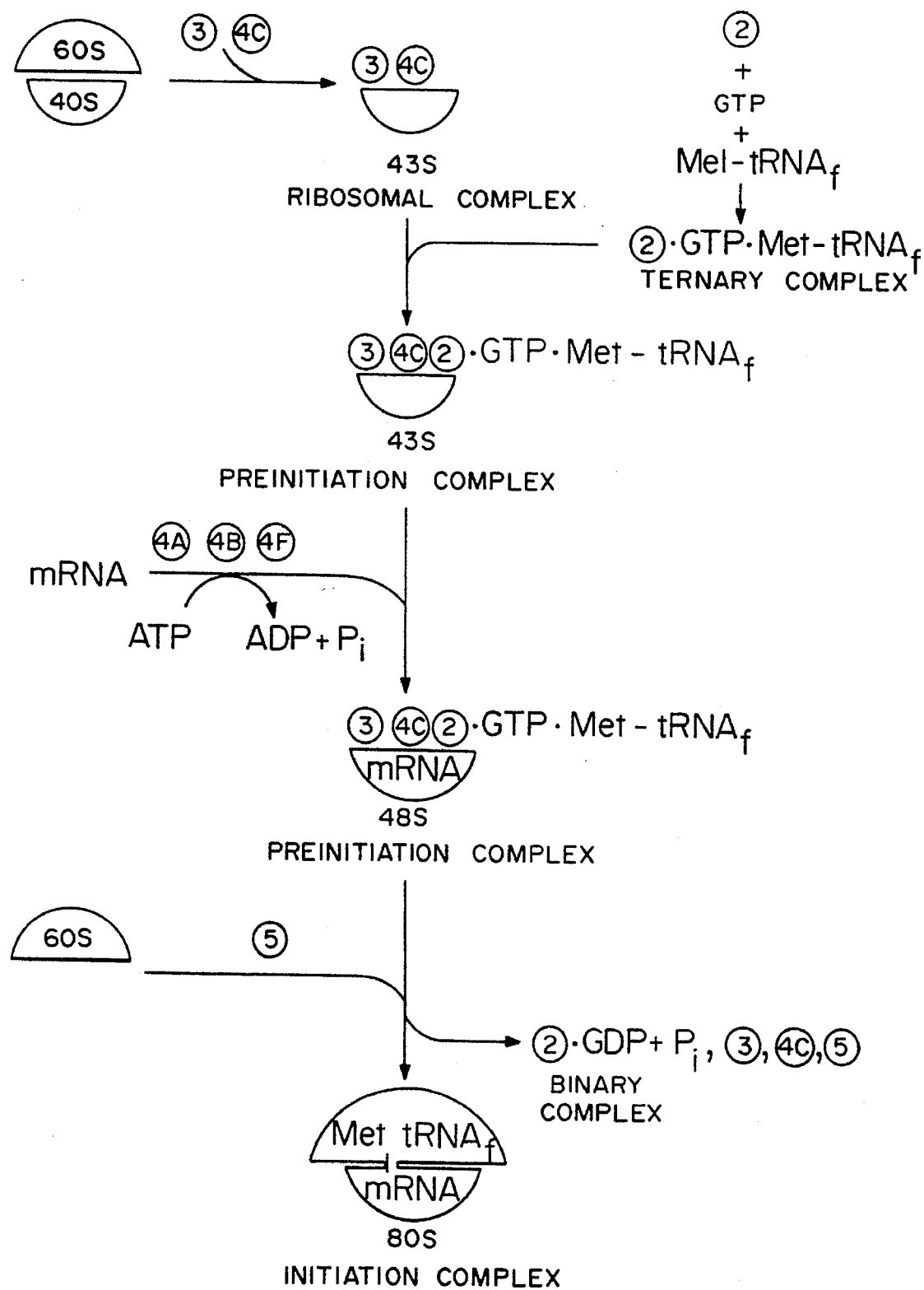
FIG. 1 is a schematic of eukaryotic initiation of protein synthesis. Numbers in circles refer to eukaryotic initiation factors.
Figure 2:
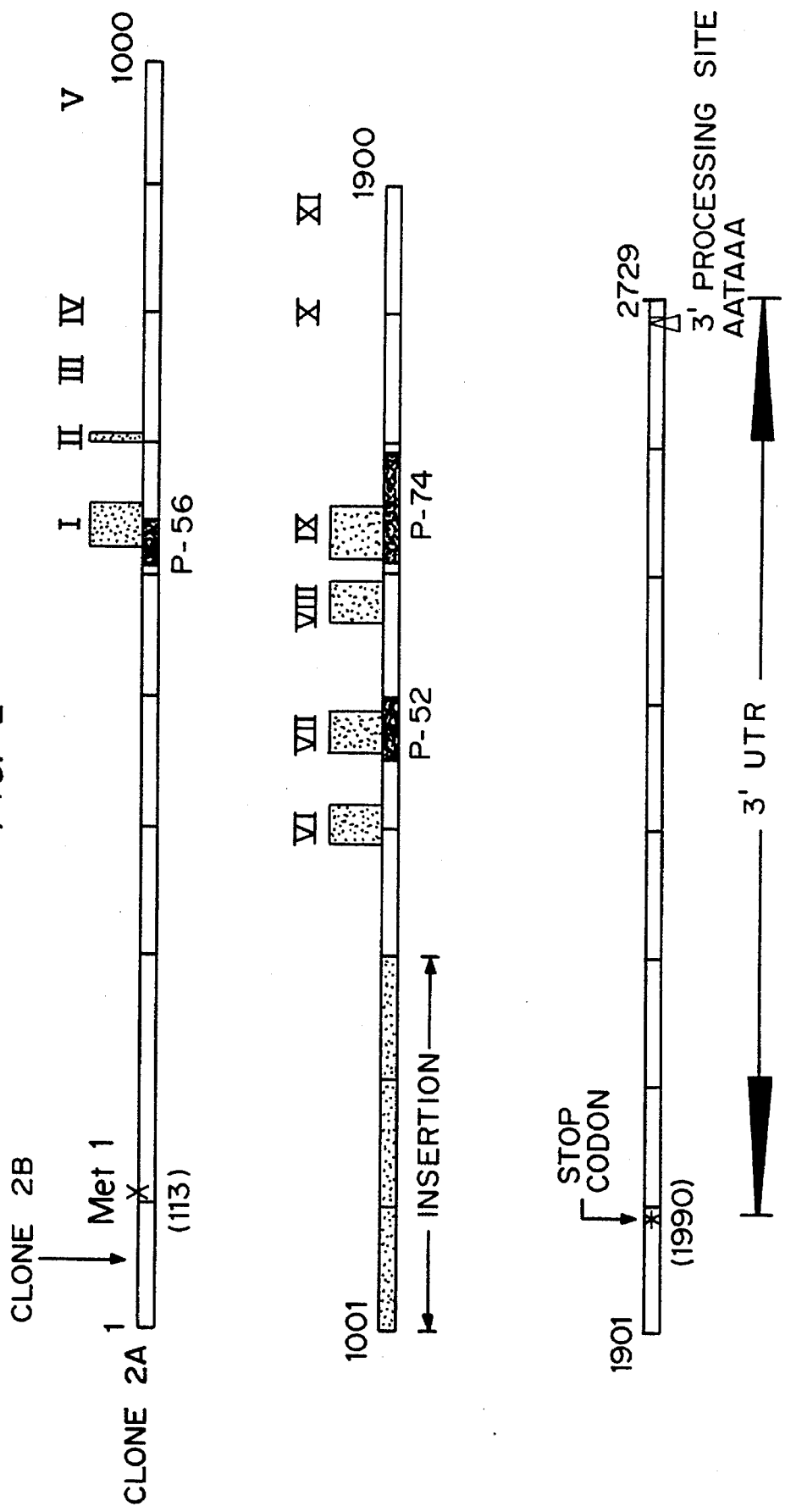
FIG. 2 is a schematic of HRI cDNA indicating the locations of the eleven domains, the HRI specific insertion region, and the three peptides previously sequenced and identified as unique to HRI: P-52, corresponding to amino acids 454 to 467, containing Asp-Phe-Gly, which is the most highly conserved short stretch in catalytic domain VII of protein kinases; P-74, corresponding to amino acids 506 to 525, containing the conserved amino acid residues Asp-(Met)-Tyr-Ser-(Val)-Gly-Val found in catalytic domain IX of protein kinases, and P-56, corresponding to amino acids 166–178.
Figure 4A:
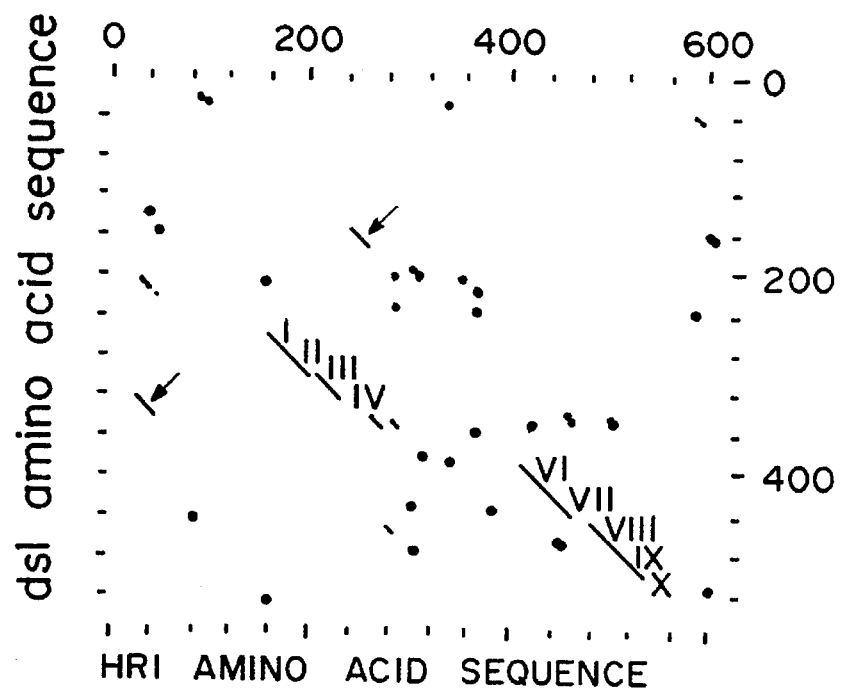
Figure 4B:
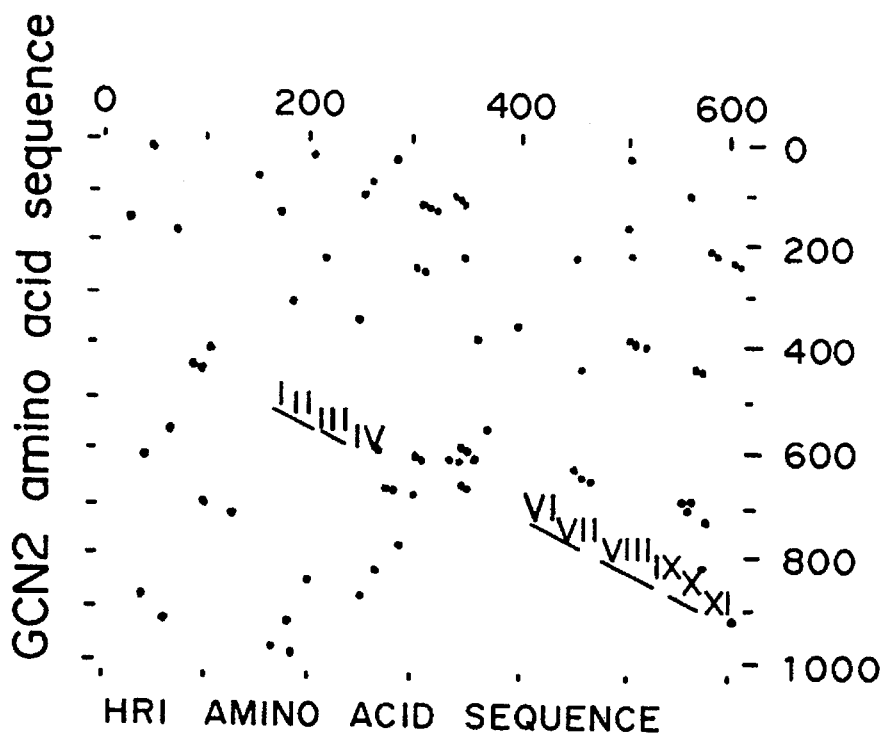

FIGS. 4A and 4B are dot-matrix analyses showing homology. (4A) Dot-Matrix analysis of the amino acid sequences of HRI and GCN2. (4B) Dot-Matrix analysis of the amino acid sequences of HRI and dsI. The dot-matrix was performed using Compare program of Maizel, J. V., Jr. and Lenk, R. P., Proc. Natl. Acad. Sci., USA 78:7665–7669 (1981), with window of 30 and stringency of 15. The locations of the conserved catalytic domains of protein kinases are indicated.

Figure 5A:
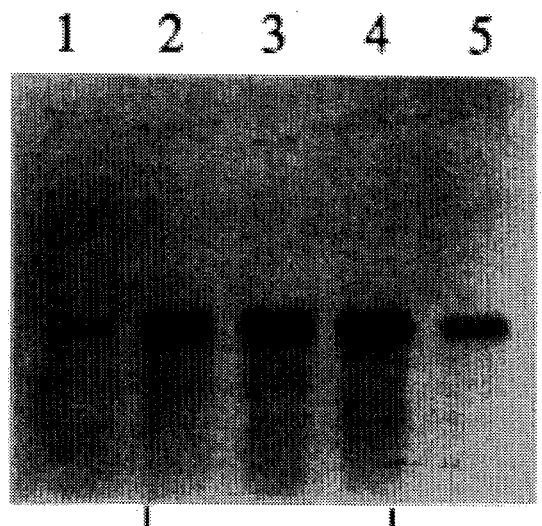

FIG. 5A is a photograph of a Northern blot showing expression of HRI mRNA in mouse erythroid cells, using as the probe rabbit HRI cDNA from nucleotides 113 to 2149 (all HRI coding sequences and 159 nucleotides of 3' noncoding sequence).

Figure 5B:
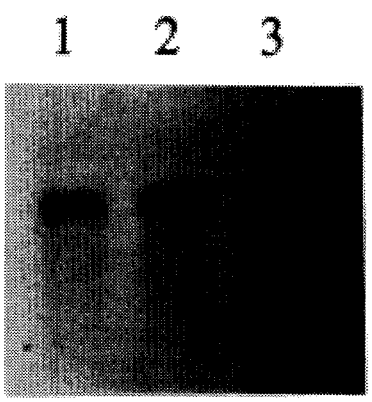

FIG. 5B is a photograph of a Northern blot showing expression of HRI mRNA in human erythroid cells, using the same probe as in FIG. 5A.

Figure 6:

FIG. 6 is a photograph of an agarose gel showing amplification of a human HRI cDNA sequence using the rabbit HRI cDNA sequence: lanes 1–3, primers were nucleotides 229–249 and 543–560; lanes 4–6, primers were nucleotides 448–468 and 1009–1031.

DETAILED DESCRIPTION OF THE INVENTION

HRI cDNA was cloned from a lambda Zap II cDNA library of rabbit reticulocytes. As described in more detail below, this cDNA is highly homologous to human DNA encoding HRI and has been used to obtain a clone encoding the human HRI, as well as HRI from other species such as mouse (although there appears to be slightly greater homology between rabbit and human than between rabbit and mouse HRI). The rabbit HRI cDNA contains 2729 nucleotides and encodes 626 amino acids. The nucleic acid sequence has been deposited in the Gene Bank data base (accession No. M69035). In vitro translation of HRI mRNA transcribed from HRI cDNA yields a 90 kDa polypeptide with eIF-2α kinase activity. This 90 kDa polypeptide is recognized by anti-HRI monoclonal antibody. These properties are characteristic of authentic HRI.

The open reading frame sequence of the HRI cDNA contains all eleven catalytic domains of protein kinases with consensus sequences of serine/threonine protein kinases in conserved catalytic domains VI and VIII. The HRI cDNA also contains an insert of approximately 140 amino acids between catalytic domains V and VI. The HRI cDNA coding sequence has extensive homology to GCN2 protein kinase of *S. cerevisiae* and to human double stranded RNA-dependent eIF-2α kinase. It therefore is believed that GCN2 protein kinase may be an eIF-2α kinase in yeast. Recently, it has been shown that phosphorylation of e2F-2α by GCN2 is required for the translational control of yeast GCN4, Dever, et al., Cell 28: 585–596 (1992).In addition, HRI has an unusually high degree of homology to three protein kinases, Nim A, Weel and CDC2, which are involved in the regulation of the cell cycle.

Isolation and sequencing of cDNA encoding HRI from rabbit reticulocytes.

PCR Amplification of HRI cDNA between P-52 and P-74.

Poly A+mRNA (1 μg) was reverse-transcribed to obtain single stranded cDNAs according to the method of Frohman, M. A., Dush, M. V. and Martin, G. R., (1988) *Proc. Natl. Acad. Sci.* USA, 85, 8998–9002. The sense-strand oligo-deoxynucleotide of P-52 and the antisense-strand oligo-deoxynucleotide of P-74, deduced with preferred codon usage as in Lathe, R., (1985) *J. Mol. Biol.*, 183. 1–12, were used as primers. The PCR reactions were carried out in the presence of single stranded cDNA template and each primer (1 μM) for 40 cycles (94° C.×1 min, 47° C.×2 min and 72° C.×3 min).

Preparation of lambda Zap II cDNA library of rabbit reticulocytes and the isolation of HRI cDNA clones.

cDNAs of rabbit reticulocytes were prepared using Pharmacia's cDNA synthesis kit. The cDNAs larger than 500 bp were pooled and were ligated to lambda Zap II vector (Stratagene). The cDNA library obtained has 95% recombinant efficiency. The cDNA library was hybridized at 42° C. overnight in a solution containing 5X Denhardt's solution, 6X SSPE, salmon sperm DNA (500 mg/ml), tRNA (1.7 mg/ml), 0.4% SDS plus heat-denatured nick-translated [$^{32}$P]-HRI cDNA probe ($10^6$ cpm/ml). (1×SSPE=0.18M NaCl/10 mM Na phosphate/1 mM EDTA pH 7.4; 1×Denhardt's solution=0.02% polyvinylpyrrolidone/0.02% Ficoll/0.02% BSA). The nitrocellulose was then washed three times with 6× SSPE and 0.1% SDS at room temperature for 5 minutes each, followed by washing twice at 50° C. under the same salt conditions for 10 minutes each. HRI cDNA was subcloned into pBlue Script plasmid by in vivo excision from the recombinant lambda Zap II as described by Stratagene. The DNA sequence of HRI cDNA was determined by the method of dideoxynucleotide chain termination of Sanger, et al., *Proc. Natl. Acad. Sci.*, USA, 74:5463–5467 (1977) with the modification described by Fawcett and Barlett, *BioTechniques*, 9:46–48 (1990).

It was not possible to use P-52, P-56, or P-74 alone to screen the library. In fact, only one of the oligonucleotides derived from these peptides worked in a Northern blot. It was necessary to combine two of the peptides in one of the many possible orientations in order to develop a probe that was useful in pulling out a full length clone.

The homology of the amino acid sequences of HRI tryptic peptides P-52 and P-74 to the conserved domains VII and IX of protein kinases made it possible to predict that P-52 was positioned to the N-terminal side of P-74. This information was used to design primers for PCR amplification of a partial HRI cDNA. Using these two primers, two amplified cDNA fragments which were approximately 230 bp in length were obtained.

This cDNA fragment was subcloned and sequenced. Excluding the 15 bp EcoR1 restriction sites present on both primers, the remaining 219 bp sequence encodes an open reading frame for 73 amino acids. The newly obtained 38 amino acid sequence of HRI deduced from this cDNA sequence contains the consensus sequence (Gly-Thr/Ser-X-X-Tyr/Phe-X-Ala/Ser-Pro-Glu) of serine/threonine protein kinases located in the conserved domain VIII. This observation is consistent with the finding by Pathak, et al., *Mol. Cell. Biol.*, 8:993–995 (1988), that HRI phosphorylates eIF-2α at serine -51. Furthermore, the amino acid sequences of HRI between conserved domains VII, VIII, and IX are unique to HRI.

150,000 recombinant clones were screened with the 234 bp probe of HRI. Among the 12 positive clones of the primary screen, five were full-length and contain a cDNA insert of approximately 2700 bp. The 2729 nucleotide sequence of HRI cDNA is shown below. There are 112 nucleotides preceding the first ATG. Starting from this first ATG (nt 113), the open reading frame continues to nucleotide 1990 encoding 626 amino acids followed by multiple stop codons in the 3' untranslated region of 739 nucleotides. It should be noted that the first 250 nt of HRI cDNA are very rich in GC content (80%). The nucleotide sequence of this area of HRI cDNA was finally obtained by using terminal deoxytransferase and pyrophosphatase. The overlapping repeat of the AATAAA polyadenylation signal is found at nucleotides 2689–2698, 11 nucleotides from the poly A tail. The deduced amino acid sequence of the HRI cDNA contains the exact amino acid sequences of the three tryptic peptides of HRI previously obtained by microsequencing. P-52 is located in domain VII, P-56 in domain I, and P-74 in domain IX.

The deoxynucleotide sequence (SEQ ID No: 1) and deduced amino acid sequence (SEQ ID No: 2) of HRI cDNA are shown below. The numbers to the left indicate the position of nucleotides while the numbers to the right indicate the position of amino acids. An asterisk (*) indicates the first stop codon. Portions of deduced amino acid sequences which match exactly the amino acid sequences of HRI tryptic peptides (P-52 , P-56 and P-74 ) are underlined and indicated. The overlapping and repeated polyadenylation signal sequence in the 3'-UTR, AATAAA is underlined.

```
  1                                                              CGCACGGCGC
 11  TCGCGACCCGGACGCGCGAGGAGGCGGTCCCGGAGTCGGGGAGCTGGCGGG
 62  TGGGCTGTGGTCCCCGCATTTGCGCGCGCGGGCGCCCGCGCGTGACCGGCG
113  ATGCTGGGGGGCAGCGCCGGGACCCGCGGGGGCGAAGCCGAGGGCGACGGG
     MetLeuGlyGlySerAlaGlyThrArgGlyGlyGluAlaGluGlyAspGly                17
164  GCGGGGGCGGTGGGGGCGGTGGCCCCGCCGCCCGCCATCGACTTCCCCGCT
     AlaGlyAlaValGlyAlaValAlaProProProAlaIleAspPheProAla                34
215  GAGGTGTCGGATCCCAAGTATGACGAGTCGGATGTCCCGGCAGAGCTGCAG
     GluValSerAspProLysTyrAspGluSerAspValProAlaGluLeuGln                51
266  GTGCTGAAGGAGCCGCTGCAGCAGCCAGCCTTCCCCTTCGCCGTCGCCAAC
     ValLeuLysGluProLeuGlnGlnProAlaPheProPheAlaValAlaAsn                68
317  CAGCTGCTGCTCGTCTCCCTGCTGGAGCACCTGAGTCATGTGCACGAGCCA
     GlnLeuLeuLeuValSerLeuLeuGluHisLeuSerHisValHisGluPro                85
368  AACCCGCTTCGCTCCAGACAGGTGTTTAAACTGCTCTGTCAGACCTTCATC
     AsnProLeuArgSerArgGlnValPheLysLeuLeuCysGlnThrPheIle               102
419  AAAATGGGGCTGCTGTCTTCCTTCACCTGCAGCGACGAGTTTAGCTCATTG
     LysMetGlyLeuLeuSerSerPheThrCysSerAspGluPheSerSerLeu               119
```

| | | |
|---|---|---|
| 470 | AGGCTGCATCACAACAGAGCTATTACGCATCTGATGAGGTCCGCCAGAGAG ArgLeuHisHisAsnArgAlaIleThrHisLeuMetArgSerAlaArgGlu | 136 |
| 521 | AGAGTTCGGCAGGATCCCTGTGCTGATAATTCTCATATCCAGAAAATCAGG ArgValArgGlnAspProCysAlaAspAsnSerHisIleGlnLysIleArg | 153 |
| 572 | TCGCGAGAAGTTGCCTTGGAAGCACAGACCTCACGATACTTGAATGAGTTT SerArgGluValAlaLeuGluAlaGlnThrSerArg<u>TyrLeuAsnGluPhe</u> | 170 |
| 623 | GAAGAGCTCTCCATCCTGGGGAAAGGTGGCTATGGCCGAGTGTACAAGGTC <u>GluGluLeuSerIleLeuGlyLysGlyGlyTyrGlyArgValTyrLysVal</u> | 187 |
| 674 | AGGAATAAATTAGATGGCCAGTATTATGCAATTAAAAAAATTCTGATTAAA ArgAsnLysLeuAspGlyGlnTyrTyrAlaIleLysLysIleLeuIleLys | 204 |
| 725 | GGTGCAACTAAAACAGATTGCATGAAGGTATTACGAGAAGTGAAAGTGCTG GlyAlaThrLysThrAspCysMetLysValLeuArgGluValLysValLeu | 221 |
| 776 | GCGGGCCTCCAGCACCCTAATATCGTAGGCTATCACACCGCGTGGATAGAG AlaGlyLeuGlnHisProAsnIleValGlyTyrHisThrAlaTrpIleGlu | 238 |
| 827 | CATGTCCACGTTCACGTTCAAGCAGACAGAGTTCCGATTCAGTTGCCTTCT HisValHisValHisValGlnAlaAspArgValProIleGlnLeuProSer | 255 |
| 878 | CTGGAAGTGCTCTCTGACCAGGAAGAAGACAGAGATCAATATGGTGTTAAA LeuGluValLeuSerAspGlnGluGluAspArgAspGlnTyrGlyValLys | 272 |
| 929 | AATGATGCAAGCAGCAGCTCATCCATTATTTTCGCTGAGTTCTCCCCAGAA AsnAspAlaSerSerSerSerIleIlePheAlaGluPheSerProGlu | 289 |
| 980 | AAAGAAAAATCCTCTGACGAATGTGCCGTTGAGAGTCAGAATAACAAACTG LysGluLysSerSerAspGluCysAlaValGluSerGlnAsnAsnLysLeu | 306 |
| 1031 | GTGAACTACACCACCAACTTAGTGGTGAGGGACACCGGTGAGTTTGAATCG ValAsnTyrThrThrAsnLeuValValArgAspThrGlyGluPheGluSer | 323 |
| 1082 | TCCACGGAGCGCCAAGAGAACGGCTCGATCGTGGAGCGTCAGCTACTGTTC SerThrGluArgGlnGluAsnGlySerIleValGluArgGlnLeuLeuPhe | 340 |
| 1133 | GGGCATAACTCAGACGTAGAAGAGGATTTCACGTCCGCGGAGGAATCTTCT GlyHisAsnSerAspValGluGluAspPheThrSerAlaGluGluSerSer | 357 |
| 1184 | GAGGAAGACTTAAGCGCGTTGCGGCACACAGAGGTGCAGTACCACCTGATG GluGluAspLeuSerAlaLeuArgHisThrGluValGlnTyrHisLeuMet | 374 |
| 1235 | CTGCATATCCAGATGCAGCTGTGCGAGCTGTCCCTGTGGGACTGGATCGCC LeuHisIleGlnMetGlnLeuCysGluLeuSerLeuTrpAspTrpIleAla | 391 |
| 1286 | GAGAGGAACAGGCGGAGCCGAGAGTGCGTGGACGAATCTGCCTGTCCTTAT GluArgAsnArgArgSerArgGluCysValAspGluSerAlaCysProTyr | 408 |
| 1337 | GTTATGGTCAGTGTTGCAACAAAAATTTTTCAAGAACTGGTGGAAGGTGTG ValMetValSerValAlaThrLysIlePheGlnGluLeuValGluGlyVal | 425 |
| 1388 | TTTTACATACATAACATGGGCATCGTGCACAGAGACCTGAAGCCTAGAAAT PheTyrIleHisAsnMetGlyIleValHisArgAspLeuLysProArgAsn | 442 |
| 1439 | ATTTTTCTTCATGGTCCTGATCAACAAGTGAAAATAGGAGACTTTGGTCTG IlePheLeuHisGlyProAspGlnGlnVal<u>LysIleGlyAspPheGlyLeu</u> | 459 |
| 1490 | GCCTGCGCCGACATCATCCAGAAGAATGCGGCCCGGACCAGCAGAAACGGG <u>AlaCysAlaAspIleIleGlnLysAsnAlaAlaArgThrSerArgAsnGly</u> | 476 |
| 1541 | GAGAGAGCACCCACACACACTTCCCGAGTGGGCACCTGTCTGTACGCCTCG GluArgAlaProThrHisThrSerArgValGlyThrCysLeuTyrAlaSer | 493 |
| 1592 | CCCGAGCAGTTGGAAGGATCGGAGTATGATGCCAAGTCAGACATGTACAGC ProGluGlnLeuGluGlySerGluTyrAspAlaLysSerAspMetTyrSer | 510 |
| 1643 | GTCGGCGTGATCCTGCTGGAGCTCTTCCAGCCCTTCGGGACAGAGATGGAG <u>ValGlyValIleLeuLeuGluLeuPheGlnProPheGlyThrGluMetGlu</u> | 527 |
| 1694 | CGGGCAGAGGTCCTGACGGGCGTGCGAGCTGGCCGCATACCCGACTCCCTC ArgAlaGluValLeuThrGlyValArgAlaGlyArgIleProAspSerLeu | 544 |
| 1745 | AGTAAGAGGTGCCCGGCGCAGGCCAAGTACGTCCAGCTGCTGACCAGGAGG SerLysArgCysProAlaGlnAlaLysTyrValGlnLeuLeuThrArgArg | 561 |
| 1796 | AACGCGTCCCAGCGGCCGTCCGCCCTTCAGCTGCTGCAGAGTGAGCTCTTC AsnAlaSerGlnArgProSerAlaLeuGlnLeuLeuGlnSerGluLeuPhe | 578 |
| 1847 | CAGAACTCCGCGCATGTTAACCTCACCCTACAGATGAAGATAATAGAGCAG GlnAsnSerAlaHisValAsnLeuThrLeuGlnMetLysIleIleGluGln | 595 |
| 1898 | GAAAGAGAAATCGAGGAACTCAAGAAGCAGCTGAGCCTCCTCTCCCAGGCC GluArgGluIleGluGluLeuLysLysGlnLeuSerLeuLeuSerGlnAla *** | 612 |
| 1949 | CGAGGGGTGAGGAGTGACAGGCGAGACGGAGAGCTCCCTGCCTAGCCGTCA ArgGlyValArgSerAspArgArgAspGlyGluLeuProAla | 626 |
| 2000 | CTCGGCCACGTCACAGGGGAACGTGGACTTGCACTTGCAGCAGTCAACTGG | |
| 2051 | AATGGACAATTTCAAGCCTCCTGAGGTTCAGGCGGCATAATCCTCACTTGG | |
| 2102 | AATCACTCAGCCCGCATGACTCTCCCCTCATGCTGCTCTTCCCGGAGGTAC | |
| 2153 | CTCCTGGTGACCTCCTGGTGACTGCTCCCAATTAAACTTACGCTTTTCCCT | |
| 2204 | TTCCTATTCCGCAAGTCCCATTCCTGAGCCTCCTACCTAAGCATTAACTAA | |
| 2255 | ATCTTAGGTATCGGTCTCCATTCTTTCTCCTTTGAATCCTGGCCACCTCGC | |
| 2306 | TCCTTTAGAAGCACACTCACTGCCCCGCCACCACCCAAGGCCAGGCCTGCA | |
| 2357 | CCCTGGCGCAACAGCTGCCAGTCTTAGTCCTTAGCTGCTGCTGCTGTTGCC | |
| 2408 | AGAGACACCTGCTCCGTTCACTCCCTCCAGGGTGGAAGCTCAGCCTGTGAG | |

```
2459  CAGCGCCTCTGCTCTCCCCGGCTGCAGCCCAGCGCCACTCGGGCAGGCTTC

2510  ACACGCTCACCCCAGGTGGCCTCGGAACAGCTGCGACAGCATCTCCCCGCA

2561  CCCTTCTGCCTTCTCAGCACTTGGCTCTCCAGCCAGCCTCTCCACTCACTC

2612  GTTTTTGTTTCCCGGAGCTGTCTGCCACAATGTTGGCAGTCTTCATGGACT

2663  ACTGTACGTGATTCTGCTGAATTTTAAATAAATAAACCCTGCAAATCAAAA

2714  AAAAAAAAAAAAAAAA
```

Expression and characterization of HRI from the isolated cDNA.

The 5' untranslated leader sequence of the HRI cDNA was replaced by the use of PCR to introduce a unique NcoI site (CCATGG) at the initiating methionine (nt 113), followed by ligation of the coding sequence to a vector containing the tobacco mosaic virus (TMV) untranslated leader sequence which was engineered to provide both the initiating methionine and 3'-terminal NcoI site. The introduction of the NcoI site changes the second amino acid of HRI from leucine to valine, constituting a conservative substitution.

Linearized HRI cDNAs were transcribed using T7 polymerase. In vitro translation of HRI mRNA (40 µg/ml) was carried out in the presence of [$^{35}$S]-methionine as described by Promega using nuclease-treated reticulocyte lysates or wheat-germ extracts. Protein kinase assays were carried out in 40 µreactions with 10 mCi of [g-$^{32}$P]ATP (3,000 Ci/mmol), 1.5 µof translational mixture and purified rabbit eIF-2 (1 µg) as indicated, at 30° C. (reticulocyte lysate) or 25° C. (wheat germ extract) for 10 min as described by Chen, J.-J., et al., J. Biol. Chem., 264:9559–9564 (1989).

In vitro transcription and translation were carried out in order to determine the apparent molecular size of the protein encoded by the HRI cDNA and to test for protein kinase activity. Translation of all five HRI clone mRNAs in a nuclease-treated rabbit reticulocyte lysate yielded a predominant 90 kDa product as observed by SDS-PAGE.

The nucleotide sequence data demonstrate that the 5' untranslated leader sequence is extremely G-C rich with the potential to form significant secondary structure. Secondary structure at the 5'-terminus of mRNAs is known to diminish mRNA translational efficiency. The HRI mRNA was not translatable in a wheat germ extract. Unlike the reticulocyte lysate, the wheat germ extract does not contain an endogenous HRI enzyme; therefore, expression of the HRI protein in the wheat germ system should facilitate analysis of kinase activity in the HRI translation products. The translational efficiency of mRNA transcripts can be increased by the use of untranslated leader sequences of some plant viral RNAs such as TMV have been shown to act in cis by Gallie, et al., (1987) Nucl. Acids Res., 15: 8693–8711, and Gehrke, L. and Jobling, S. A., (1990) In: McCarthy, JEG Post-Transcriptional Regulation of Gene Expression, Series H: Cell Biology, ed. Tuite, M. (Springer Verlag, Berlin), Vol. 49, pp. 389–398. Accordingly, the G-C rich HRI untranslated leader sequence was replaced with that of TMV. The chimeric TMV-HRI mRNA was translated with approximately tenfold greater efficiency than HRI mRNA in the reticulocyte lysate, and translation in the wheat germ extract was clearly evident. In all cases, the translated product of HRI mRNA migrated slightly faster than authentic purified phosphorylated HRI on SDS gel electrophoresis. This slight difference in mobility is most likely due to a lower level of phosphorylation in the translation products.

To determine whether the translational product derived from the mRNA of HRI cDNA is an eIF-2α kinase, a small portion of the total translation mixture was incubated with purified rabbit reticulocyte eIF-2 and [g-$^{32}$P] ATP in the absence of added hemin under protein kinase assay conditions and analyzed by SDS-gel electrophoresis.

The results show that translational products of HRI 2A and HRI 2B mRNAs have enhanced eIF-2α kinase activity as compared to the control in the absence of added mRNA. It should be emphasized that under the kinase assay conditions (final hemin concentration of 0.75 µM) the activity of newly synthesized HRI exceeds the low activity of endogenous pre-formed HRI in the nuclease-treated lysate and makes it possible to detect enhanced phosphorylation of eIF-2α. In the absence of added purified rabbit eIF-2, only slight phosphorylation in the region of eIF-2α is observed. Furthermore, the HRI polypeptide synthesized in the wheat-germ extracts exhibits eIF-2α kinase activity as does purified HRI. It should be noted that there is no mammalian eIF-2α kinase activity in the wheat-germ extracts, and the purified reticulocyte HRI phosphorylates purified wheat germ eIF-2α very inefficiently. In addition, the 90 kDa polypeptide expressed from HRI cDNA is immunoprecipitated by monoclonal antibodies to HRI.

Isolation of cDNA encoding HRI in other mammalian species.

DNA nucleotide sequence data were analyzed in part using CAD Gene™ software for the Macintosh™ computer, provided by the Genetic Technology Corporation, Cambridge, Mass. The amino acid sequences of dsRNA-dependent eIF-2α kinass (dsI) of rabbit and human are 83% similar and 76% in identity. Similar or higher degree of homology of initiation factors (eIF-2α, and eIF-2 eIF-4A, eIF-4E, EF-1a) between human and rabbit has been demonstrated. The predicted homology of HRI between human and rabbit is greater than 80%. Accordingly, the sequence encoding HRI in human or other species can be isolated by hybridization under standard conditions such as those outlined by Maniatis, et al., (1989) Molecular Cloning. A Laboratory Manual, from a library prepared from reticulocytes of the other species. The isolated sequence can then be expressed in the same manner as the HRI cDNA isolated from rabbit reticulocytes as described below in the Examples.

High degree of homology between HRI and other protein kinases.

Purified non-recombinant HRI undergoes hems-regulated autophosphorylation and eIF-2α phosphorylation. The sites of autophosphorylation of many protein kinases are located within 20 amino acids of the conserved Ala/Ser-Pro-Glu sequence in catalytic domain VIII (e.g. Thr-197 of cAMP-dependent protein kinase). The HRI-equivalent of the Thr-197 of cAMP-dependent protein kinass is Thr-483. In addition, there are two serine and three more threonine residues in the vicinity of Thr-483. Since HRI can undergo multiple phosphorylation in vitro the availability of HRI cDNA will facilitate the further study of the sites and role of autophosphorylation in the activation of HRI.

Comparison of HRI and dsI and GCN2 protein kinase.

Comparison of the amino acid sequences of HRI and dsI deduced from the cDNAs indicates that in addition to general homology in kinase conserved domains, there is a very significant homology of both eIF-2α kinases around domains IX and X (HRI amino acid 511–540), as shown in FIG. 4A. It is likely that these amino acids are involved in eIF-2 binding and the phosphorylation of eIF-2α. In addition, HRI synthetic peptide P-74 which resides around domain IX inhibits the eIF-2α kinase activity of both HRI and dsI.

The Gene Bank has been searched for homology to other protein sequences of the amino acid sequence of HRI deduced from its cDNA. Of the ten proteins with the highest scores (Table I), nine are Ser/Thr protein kinases, and of these, three are involved in regulation of the cell cycle (Nim A, Weel and CDC2).

It is especially noteworthy that GCN2 protein kinase of yeast displays more homology to HRI than does dsI, the other known eIF-2α kinase (Table I). The scores of homology of HRI to GCN2 and dsI are significantly higher than those to other protein kinases (Table I). The cDNA of human dsI was recently cloned by Meurs, et al., (1990) *Cell, 62:379–390*. A dot-matrix homology analysis of HRI and dsI coding sequences is shown in FIG. 4A, and a similar analysis of HRI and the kinase moiety of GCN2 coding sequences is shown in FIG. 4B. These dot-matrix plots reveal the extensive homology of these three proteins in the protein kinase catalytic domains I through X except for domain V where HRI has a large kinase insertion sequence. Homology in domains IX and X is observed only with HRI, dsI and GCN2, but not with the other eight protein kinases with the best scores. The significant homology in these regions suggests that these amino acids may be involved in the binding and phosphorylation of eIF-2, and raise the possibility that GCN2 protein kinase may be an eIF-2α kinase in yeast.

TABLE 1

Homology of HRI to other Protein Kinases

| Kinase | Scores |
|---|---|
| GCN2 protein kinase (Yeast) | 383 |
| dsRNA-dependent eIF-2α kinase (Human) | 331 |
| $Ca^{+2}$/calmodulin protein kinase (Rat) | 252 |
| Never-in-Mitosis gene product (Yeast) | 249 |
| Wee 1 gene product (Yeast) | 246 |
| Type II $Ca^{+2}$/calmod kinase (Rat brain) | 222 |
| Calmodulin-dependent protein kinase (Rat) | 211 |
| Calmodulin-dependent protein kinase II (Rat) | 211 |
| M38724 Mus musculus cell cycle protein | 209 |
| Calmodulin-dependent protein kinase II (Rat) | 207 |
| CDC2 gene product (Human) | 206 |
| cAMP-dependent protein kinase (Yeast) | 205 |
| Protein kinase gene (Yeast) | 205 |
| M37712 p58/GTA protein kinase (Human) | 204 |
| cAMP-dependent kinase (Yeast) | 197 |
| TPK2 gene (Yeast) | 195 |
| cAMP-dependent kinase | 194 |
| Protein Kinase C (Rat) | 192 |
| Protein kinase C zeta-subspecies (Rat) | 184 |
| CDC2 cell division gene (Yeast) | 184 |
| Varicella-Zoster virus complete genome | 181 |
| Muscle light chain kinase (Rat) | 180 |
| HSV-2 genomic HindIII 1 region | 180 |
| Tyrosine kinase (Rat) | 180 |
| Src (Rat) | 180 |
| Tyrosine kinase (Human) | 176 |

The homology of the protein sequence of HRI to those of other proteins in Gene Bank was determined using Fast A program of Pearson, W. R. and Lipman, D. J., (1988) Proc. Natl. Acad. Sci., USA, 85:2444–2448. A score of 300 to 400 indicates approximately 50% homology, whereas a score of 200 indicates approximately 25% homology.

GCN2 protein kinase of yeast displays very significant homology to HRI (Table I and FIG. 4B) especially in domains IX and X in which considerable homology is observed only in eIF-2α kinases. GCN2 protein kinase stimulates the expression of amino acid biosynthetic genes under conditions of amino acid starvation by derepressing GCN4, a transcriptional activator of these genes. The derepression of GCN4 by GCN2 protein kinase occurs at the level of translation of GCN4 mRNA. The activation of the translation of GCN4 mRNA coincides with a decrease in the rate of general polypeptide chain initiation at the level of eIF-2 dependent 43 S pre-initiation complex formation. Furthermore, a yeast strain that overexpresses GCN2 protein kinase has been reported to have a lower rate of protein synthesis. Thus, the effect of GCN2 protein kinase on protein synthesis is very similar to that of HRI. The molecular cloning of yeast eIF-2α by Cigan, et al., (1989) *Proc. Natl. Acad. Sci.*, USA, 86:2784–2788, reveals 58% homology of its amino acid sequence to human eIF-2α, as reported by Ernst, et al., (1987) *J. Biol. Chem.*, 262:1206–1212. In addition, consensus phosphorylation site Ser-51 is conserved in yeast eIF-2α, and the phosphorylation of yeast eIF-2α has been demonstrated by Cigan, et al. The possibility that GCN2 protein kinase may phosphorylate eIF-2 has been raised by Cigan et al and Tzamarias et al, (1989) *Cell*, 57:947–954. The alignment of the amino acid sequences of HRI and GCN2 indicates 52% similarity and 28% identity in the kinase moiety of GCN2. This extensive homology of HRI and GCN2 affords further support for the view that GCN2 may be an eIF-2α kinase in yeast. Recently, it has been demonstrated that phosphorylation of e2F-2α is required for the translational control of yeast GCN4, Dever, et al., *Cell 68:585–596* (1992).

Comparison of unique insertion Sequence.

As shown in FIG. 4, HRI cDNA contains an insertion of approximately 140 amino acids between catalytic domains V and VI (amino acids 276 to 413). Similar large inserts have been reported for subclass III and IV receptor tyrosine kinases, which include the PDGF receptor, the CSF-1 receptor and the c-kit proto oncogene product, in which the kinase domains are divided into two halves by insertion of up to 100 mostly hydrophilic amino acid residues, as reviewed in Ullrich, A. and Schlessing, J., (1990) *Cell*, 61:203–212. Since kinase insertion sequences are highly conserved among species for each specific receptor, the kinase insert may play an important role in the action of receptor kinases. Indeed, the PDGF receptor kinase insert contains an autophosphorylation site (Tyr-751), and mutation of Tyr-751 to Phe or Gly blocks association of the PDGF receptor with phosphatidylinositol kinase and three other cellular proteins. In the case of HRI, heme binds to HRI and regulates its kinase activities. It is believed that the kinase insertion sequence of HRI is involved in the binding of heme and the regulation of the autokinase and eIF-2α kinase activities.

Comparison of HRI and protein kinases involved in the cell cycle.

There is also a high degree of homology between HRI and several protein kinases involved in the cell cycle.

Hanks, Quinn and Hunter (1988) *Science, 241:42–52*, have compared and aligned the protein sequences of 65 different protein kinases. They have identified eleven domains of protein kinases with invariant amino acid residues in each domain. The alignment of the HRI sequence with the sequences of a serine/threonine protein kinase ($Ca^{++}$/calmodulin protein kinase) and of a tyrosine protein kinase (Src) is shown in FIG. 3. HRI cDNA contains all eleven catalytic domains with invariant amino acid residues, as also shown in FIG. 4. The consensus ATP-binding sequence, Gly-X-Gly-X-X-Gly, and the invariant valine residue located two positions downstream of the Gly-X-Gly- X-X-Gly are conserved in HRI. In domain II, the invariant Lys residue has been shown to be indispensable and to be involved in the phosphotransferase activity of protein kinases. In HRI this invariant residue is Lys-199. Domain VI contains the consensus sequence which specifies either Ser/Thr protein kinases or Tyr protein kinases. HRI possesses Asp-Leu-Lys-Pro-Arg-Asn in domain VI which is characteristic of Ser/Thr protein kinases. Asp-Phe-Gly located in domain VII is the most conserved short stretch in the catalytic domains of protein kinases and is probably involved in ATP-binding. It is found in HRI as Asp(-456)-Phe(-457)-Gly(-458). In domain VIII the Ala/Ser-Pro-Glu consensus sequence essential for catalytic activity of protein kinases is also found in HRI. Domain VIII of HRI contains the other consensus sequence for Ser/Thr protein kinases, Gly-Thr-Cys-Leu-Tyr. The conserved amino acids in domain IX are also found in HRI. Thus, the homology of the deduced amino acid sequence of HRI cDNA to the conserved domains of other Ser/Thr protein kinases provides confirmatory evidence that HRI cDNA encodes a Ser/Thr protein kinase.

Inhibition of Cell Proliferation and Differentiation and vital activity and the induction of Differentiation using HRI or dsI.

Since HRI is a potent inhibitor of protein synthesis, it is anti-proliferative in nature and should be useful in the treatment of various cancers in which uncontrolled cell growth persists, for example chronic myelogenous leukemia. HRI should also be useful in treatment of other proliferative disorders such as psoriasis.

Initiation of protein synthesis can also be regulated by another eIF-2α kinass which is activated by double-stranded RNA (dsI). Both HRI and dsI phosphorylate eIF-2α at the same site. However, HRI and dsI are different molecules. dsI is induced by interferon and represents an interferon mediated response to viral infection. However, mechanisms of inactivating dsI have evolved in various viruses to undermine the anti-viral action of dsI. Since HRI and dsI are both eIF-2α kinases, both should be anti-viral in nature. However, mechanisms of inactivating viruses by dsI should not similarly affect HRI activity. Therefore, when introduced into the proper target cell, HRI may be as potent or more potent than dsI as an anti-viral agent.

Based on the similarity to proteins involved in cellular differentiation, it is expected that HRI will induce differentiation. As noted above, CDC2, Wee 1 and Nim A contain consensus sequences for serine/threonine protein kinases. They were identified first in yeast by genetic means. However, CDC2 and Wee 1 have also been isolated and characterized in human cells. The CDC2 gene product is required for both S phase and mitosis. The Wee 1 gene product is an inhibitor of mitosis. Nim A gene product is an activator of mitosis. Both Nim A and Wee 1 gene products regulate the cell cycle through regulation of CDC2 kinase which is part of the mitosis promoting factor. Many types of cancers are characterized by arrested differentiation. HRI can also be introduced into these cells to induce differentiation and thereby limit the proliferation of the transformed cells.

Since HRI is expressed normally only in very small quantities, in the cytoplasm, and during specific periods of erythroid differentiation, small quantities of the protein are expected to be effective in inhibiting protein synthesis, inducing differentiation, and inhibiting infection by viruses and parasites.

The HRI, expressed from the cDNA, preferably of the same species as the cells to be treated, can be administered topically, by injection, or via implant to the cells or patient to be treated. Appropriate pharmaceutical compositions and methods for administration and use thereof are well known to those skilled in the art. The HRI can be expressed in any suitable mammalian expression system, using known technology, under the control of appropriate enhancers and promoters.

Alternatively, the cells to be treated are "infected" with the sequence encoding the HRI. In the preferred embodiment, this is accomplished by inserting the HRI sequence into a retroviral vector with which the cell is then infected. For example, a retroviral vector for gene transfer and expression of HRI cDNA can be constructed using as the backbone of the retroviral vector the LNCX vector described by Miller and Rosman (Miller, A. D., and Rosman, G. J. (1989) *BioTechniques* 7:980–990). It contains human cytomegalovirus (CMV) immediate early gene promoter and enhancer. HRI cDNA containing TMV-leader sequence is introduced into the LNCX vector through a polylinker region downstream from the CMV promoter.

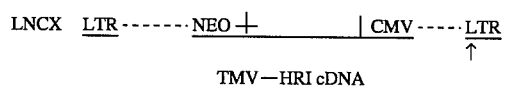

TMV—HRI cDNA

Gene transfer by retroviral vector can also be achieved by transfection by a viral vector, using the method of Wilson, J. M. Biriuyi, L. U., Salomon, R. U., et al. Transplantation of Vascular Grafts Lined With Genetically Modified Endothelial cells. *Science*, 244:1344–1346 (1980), or a plasmid transfer technique, as described by Felgner, P. L., Galik, T. R., Holmer, et al. Lipofection: An Efficient, Lipid Mediated DNA-Transfection Procedures. *Proc. Natl. Acad. Sci.*, 84:7413–7417 (1987), the teachings of which are incorporated herein by reference.

Specifically, cells are harvested, grown to subconfluence (60–70%) and incubated with a replication defective murine Moloney leukemia retroviral vector. The DNA sequence for HRI is inserted into the viral genome and is under the promoter control of the viral long-terminal repeats (LTR's). The infected cells are trypsinized, resuspended in saline containing penicillin (100 µ/ml) and streptomycin (100 µg/ml) and transplanted into the patient requiring treatment. The presence of HRI in the culture medium or the site of transplantation can be determined by radioimmunoassay.

Construction of deletion mutants of HRI cDNA that are insensitive to hems, less species specific or overexpressed.

Deletion mutants of HRI cDNA which are not sensitive to regulation by hems can be constructed, based on the prediction that the hems-binding region is found within the HRI-specific insert discussed above and/or in the 170 N-terminal amino acids. This hems-insensitive HRI may be more effective than native HRI in its anti-viral and anti-proliferative action.

Deletion mutants of HRI cDNA can also be constructed which are less species specific. There is greater than 80% homology between species (86% between human and rabbit dsI). The primary area of species variation is in domain V. Methods for constructing and screening for these mutations are known to those skilled in the art.

EXAMPLE 1

Expression of HRI mRNA in Human and Mouse Erythroid Cells.

The expression of HRI mRNA in human erythroleukemia cells (K562) and mouse Friend erythroleukemia cells (MEL) during erythroid differentiation was examined by Northern- Blot analysis. The probe used for the Northern-Blot analysis shown in FIGS. 5A and 5B is the above-described rabbit HRI cDNA from nucleotides 113 to 2149 which is comprised of all the coding sequences of HRI eDNA and 159 nucleotides of the 3'non-coding sequence. The results in FIGS. 5A and 5B show that rabbit HRI cDNA hybridizes to a 3.1 Kb ERNA from both MEL (Panel A) and K562 (Panel B) cells. The HRI mRNA from K562 and MEL cells appears to be of the same size as rabbit HRI mRNA. In addition, HRI mRNA is increased upon erythroid differentiation induced by incubation of cells with hemin for four days.

Cell Culture

K562 cells were maintained in RPMI 1640 medium containing 10% fetal calf serum and antibiotics at 37° C. in 5% $CO_2$. Cells were treated with 75 mM hemin by dilution of a 1 mM hemin stock solution directly into the culture medium. After four days, the cells were washed twice in culture medium and incubated in their normal growth medium for 12 hours. The cells were then collected and washed twice in phosphate buffered saline (PBS). MEL cells were grown in Dulbeco modified minimum essential medium containing 10% fetal calf serum. Cells were induced for erythroid differentiation by the addition of 2% dimethylsulfoxide (DMSO). Cells were harvested 3, 4 and 5 days after DMSO-treatment as described above.

mRNA Isolation and Northern Blotting

Poly $(A)^+$mRNA was isolated from both untreated K562 cells, hemin treated K562 cells, untreated MEL cells and DMSO-treated MEL cells using oligo (dT) cellulose and an Invitrogen™ mRNA Isolation Kit. $1 \times 10^8$ cells consistently yielded 15–20 µg of high quality mRNA. 5 µg of each sample mRNA were denatured and separated on 1.0% agarose formaldehyde denaturing gels. mRNA was transferred to a nitrocellulose membrane in 20X SSPE overnight at room temperature and cross-linked to the nitrocellulose by UV irradiation.

Hybridization

Nitrocellulose filters were prehybridized in 50% formaminde, 6×SSPE, 5×Denhardt's solution, 0.5% SDS, 100 mg/ml salmon sperm DNA and 10% dextran sulfate, at 42° C. for overnight (12–14 hrs). Hybridization took place under the same conditions but for the addition of $1-3 \times 10^9$ cpm/µg $^{32}$P-labeled HRI cDNA. Nitrocellulose filters were washed 3 times for 5 minutes in 2× SSPE+0.1% SDS at room temperature (R.T.), followed by washes of 1×SSPE+0.1% SDS for 10 minutes at room temperature, 1×SSPE+0.1% SDS for 10 minutes at 50° C., and 0.2× SSPE +0.1% SDS for 10 minutes, film (Kodak X-AR) at −80° C. with an intensifying screen.

EXAMPLE 2

Amplification of Human HRI cDNA Sequence Using Rabbit HRI cDNA Sequence.

Several oligonucleotides of the above-described rabbit HRI cDNA were used as primers for the polymerase chain reaction (PCR) to amplify the human HRI cDNA sequence. The poly $A^+$mRNAs from hemin-induced K562 cells was reversed-transcribed to obtain single-stranded cDNAs. This single-stranded cDNA preparation was used as a template to amplify a human HRI cDNA sequence. The primers used for PCR reactions shown in Lanes 1 to 3 of FIG. 6 are nucleotides 229–249 and nucleotides 543–560. An expected DNA fragment of 331 bp was amplified from cloned HRI cDNA 2B of rabbit (Lane 3). A faint but detectable DNA fragment of the same size was also amplified from the cDNA reversed-transcribed from human K562 poly $A^+$mRNA (Lane 2), but not from human HeLa cells (Lane 1). The primers used for PCR reactions shown in Lanes 4 to 6 are nucleotides 448–468 and nucleotides 1009 to 1031. An expected DNA fragment of 584 bp was amplified from cloned rabbit HRI cDNA 2B (Lane 6) and from human K562 cDNA (Lane 5). These two amplified human HRI cDNA fragments are located in the N-terminus of HRI coding sequence where conserved sequences of protein kinase are not found. The lack of homology of the N-terminus of HRI to other nucleotide sequences is shown in Table 2. The N-terminus of protein kinases is usually devoted to a regulatory role of a particular protein kinase. The result of a search of the GeneBank database indicates that the first 170 amino acids of the N-terminus of HRI is unique to HRI; no significant homology to other eIF-2α kinases (GCN2 and dsI) is observed. Therefore, the amplification of human HRI cDNA sequences from rabbit HRI cDNA shown in FIG. 6 is very significant and demonstrates the extensive homology of human HRI cDNA to rabbit HRI cDNA. The human HRI cDNA sequence in the conserved domains from domain VII to domain IX was also amplified.

TABLE 2

| Non-Homology of N-terminus of HRI to other Kinases | |
| --- | --- |
| Kinase | Scores |
| Varicella-Zoster virus complete genome | 100 |
| Skeletal muscle voltage-sensitive Na+ channel (Rat) | 96 |
| Cytomegalovirus (HCMV) (Human) | 92 |
| Foot and Mouth Disease Virus | 92 |
| Adenylate cyclase gene | 90 |
| cGMP-dependent protein kinase (D. melanogaster) | 88 |
| Mesothelial keratin K7 (type II) (Human) | 88 |
| Mei2 gene (Human) | 86 |

The non-homology of the protein sequence of the N-terminal of HRI to other sequences in Gene Bank was determined using Fast A program of Pearson, W. R. and Lipman, D. J., (1988) Proc. Natl. Acad. Sci., USA, 85:2444–2448. A score of 300 to 400 indicates approximately 50% homology, whereas a score of 200 indicates approximately 25% homology.

The results of FIGS. 5A, 5B and 6 demonstrate that HRI cDNA from species other than rabbits, including humans, can be cloned using rabbit HRI cDNA from a cDNA library of hemin-treated K562 cells.

Modifications and variations of the present invention, the cDNA encoding HRI, and methods of use thereof, will be obvious to those skilled in the art from the foregoing detailed description. Such modifications and variations are intended to come within the scope of the following claims.

We claim:

1. An isolated mammalian DNA sequence encoding heme-regulated eukaryotic initiation factor 2α (EIF-2α) kinase which specifically hybridizes to primers consisting of nucleotides 22–249, 448–468, 543–560 or 1009–1031 of SEQ ID NO:1.

2. The sequence of claim 1 wherein the first 170 amino acids of the protein are encoded by a DNA sequence including nucleotides 113 to 622 of Sequence Linsting ID No. 1.

3. The sequence of claim 1 encoding human heme-regulated eukaryotic initiation factor 2α kinase.

4. The sequence of claim 1 encoding rabbit heme-regulated eukaryotic initiation factor 2α kinase.

5. The sequence of claim 1 further comprising a promoter and enhancer operably linked to permit expression in mammalian expression system.

6. The sequence of claim 4 further comprising a cloning vector for expression in a mammalian cell.

* * * * *